(12) United States Patent
McDonald et al.

(10) Patent No.: US 9,708,323 B2
(45) Date of Patent: Jul. 18, 2017

(54) TRICYCLIC COMPOUNDS AS ALPHA-7 NICOTINIC ACETYLCHOLINE RECEPTOR LIGANDS

(71) Applicant: BRISTOL-MYERS SQUIBB COMPANY, Princeton, NJ (US)

(72) Inventors: Ivar M. McDonald, East Haddam, CT (US); F. Christopher Zusi, Hamden, CT (US); Richard E. Olson, Orange, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/317,546

(22) PCT Filed: Jun. 5, 2015

(86) PCT No.: PCT/US2015/034569
§ 371 (c)(1),
(2) Date: Dec. 9, 2016

(87) PCT Pub. No.: WO2015/191403
PCT Pub. Date: Dec. 17, 2015

(65) Prior Publication Data
US 2017/0137425 A1    May 18, 2017

Related U.S. Application Data

(60) Provisional application No. 62/011,635, filed on Jun. 13, 2014.

(51) Int. Cl.
*C07D 471/18* (2006.01)

(52) U.S. Cl.
CPC ................... *C07D 471/18* (2013.01)

(58) Field of Classification Search
CPC ....................................... C07D 471/18
USPC ....................................... 514/214.2
See application file for complete search history.

(56) References Cited

FOREIGN PATENT DOCUMENTS

DK    WO 2007093601 A1 *  8/2007  ........... C07D 471/08

* cited by examiner

*Primary Examiner* — Yevegeny Valenrod
(74) *Attorney, Agent, or Firm* — James Epperson

(57) ABSTRACT

The disclosure provides compounds of formula I including their salts, as well as compositions and methods of using the compounds. The compounds are ligands for the nicotinic 7 receptor and may be useful for the treatment of various disorders of the central nervous system, especially affective and neurodegenerative disorders.

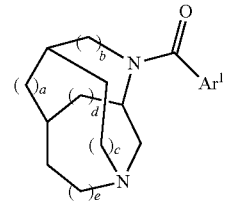

12 Claims, No Drawings

TRICYCLIC COMPOUNDS AS ALPHA-7 NICOTINIC ACETYLCHOLINE RECEPTOR LIGANDS

CROSS-REFERENCE TO RELATED APPLICATIONS

This application claims priority to U.S. Provisional Patent Application Ser. No. 62/011,635, filed Jun. 13, 2014, which is incorporated by reference in its entirety.

BACKGROUND OF THE INVENTION

The disclosure generally relates to compounds of formula I, including their salts, as well as compositions and methods of using the compounds. The compounds are ligands, agonists and partial agonists for the nicotinic α7 receptor and may be useful for the treatment of various disorders of the central nervous system, especially affective and neurodegenerative disorders.

Schizophrenia is a serious mental disorder, affecting approximately 1% of the population. Its progressive course results in major impairment of mental and social functioning and often leads to the development of other pathologies. Susceptibility often runs in families, with both genetic and environmental factors thought to be important. The direct and indirect costs of the disease are estimated in the tens of billion dollars annually in the U.S. alone.

Patients with schizophrenia have an elevated risk of suicide (approximately a 10% lifetime risk). They have a 2.5 fold increase in all-cause mortality, resulting in a 20% lowered life expectancy. The onset of illness can result in cascade of unhealthy lifestyle factors and behaviors that elevate the risk of various conditions and consequently the risk of death.

The onset of schizophrenia is most often in late adolescence or early adulthood, and episodes recur throughout life. The disease is characterized by the expression of three distinct symptom domains: positive, negative and cognitive. Psychotic or positive symptoms include delusions, hallucinations, thought disorder and paranoia. Negative symptoms include negative affect, social withdrawal, and anhedonia. Cognitive dysfunction includes deficits in attention, working memory and executive function. The pathophysiology of schizophrenia is not well understood, however, most experts believe it is a multi-factorial disorder in which biological, genetic and environmental factors play a role. Most current therapies target the dopaminergic system and have resulted in the suggestion that an excess of dopaminergic neurotransmission underlies at least some aspects of schizophrenia. This theory received further support from findings that drugs which increase the levels of dopamine cause psychoses similar to the positive symptoms of the disease. Also, post mortem analysis of brains from schizophrenic patients indicate increased numbers of D2 dopamine receptors. Although newer antipsychotic agents, known as atypical antipsychotics, which are active at several additional neurotransmitter receptors, have been introduced in the past decade, these agents still share efficacy against the D2 dopamine receptor. All currently-used agents also have major limitations. Although positive symptoms are generally reduced in a majority of patients, these drugs do little to relieve the negative symptoms and cognitive deficits that are common and often most debilitating. In addition, antipsychotic agents have a number of unwanted and limiting side effects.

Nicotine is among the few agents which have a positive effect on cognitive function. Many schizophrenics smoke; the rate in patients is 2-4 times that of the general population, and up to 90% in schizophrenics who have been institutionalized do smoke. This smoking habit has been characterized as a form of self-medication.

Nicotinic acetylcholine receptors (nAChR's) are pentameric ligand-gated ion channels which are widely expressed through the central and peripheral nervous system. These channels are fast-desensitizing calcium channels which, when open, increase the intracellular concentration of the $Ca^{++}$ ion. Although there are 12 individual receptors, the most abundant nicotinic receptors in the brain are α4β2 and α7. The α4β2 complex has been identified as the "high affinity" nicotine site. The homo-pentameric α7 receptor selectively binds the natural product, α-bungarotoxin, which has allowed its relatively facile localization and measurement. The α7 receptor is primarily expressed in the cortex, hippocampus and subcortical limbic regions and commonly occurs pre-synaptically. The localization of α7 nAChRs in areas involved with learning and memory has led to studies using both knockout mice and pharmacological manipulation. It is involved in sensory gating, memory, and neuronal plasticity. Alpha7 agonists have been shown to increase the release of neurotransmitters in rodents, including dopamine, serotonin, glutamate and GABA. Compounds which selectively bind to the α7 receptor, such as α7 agonists and partial agonists, have been shown to improve learning and memory functions in normal and aged animals, reverse scopolamine-induced memory deficits, reverse deficits in cognition induced by NMDA antagonists, reverse pharmacologically-induced gating deficits, e.g. amphetamine induced gating disruption, and to possess some anxiolytic properties. The α7 agonists of the present invention are expected to be useful in the treatment of schizophrenia and cognitive disorders associated with schizophrenia.

Alzheimer's disease is a progressive neurodegenerative disorder, resulting in the general loss of cognitive functions. The incidence increases with age, to the degree that 25-50% of all individuals over 85 are estimated to suffer from some degree of dementia. A diagnosis of Alzheimer's implies that the remaining life expectancy is reduced by half, compared to normal adults.

Clinical signs of Alzheimer's disease are progressive cognitive deterioration, decreased ability to perform the activities of daily living and neuropsychiatric symptoms or behavioral changes. In the advanced stages of the disease, deterioration of musculature and mobility may lead to inability to feed oneself, and eventually to the patient becoming bedridden. Language becomes severely disorganized, and then is lost altogether. Patients are not able to perform even simple tasks independently and require constant supervision. The cost of institutional care makes up nearly 70% of the cost of the disease. Therefore, therapies which increase cognitive function and delay institutionalization are greatly needed.

Alzheimer's disease has been shown in several studies to be accompanied by a reduction in nicotinic receptors in the cortex and hippocampus. Nicotine injections or nicotine skin patches have been reported to significantly improve attention, memory and learning in Alzheimer's disease patients. While there is a progressive loss of nicotinic receptors during the course of Alzheimer's disease, the α7 neurons are relatively spared, compared to the more abundant α4 receptors. Recently, the administration of selective nicotinic α7 agonists has been shown to increase cognitive functioning in Alzheimer's patients when dosed as long as 8 weeks. This clinical data is consistent with pre-clinical data showing α7 agonists and partial agonists improve learning and memory functions in normal and aged animals and reverse scopolamine-induced memory deficits. Thus, the compounds of the present invention may be useful in the treatment and prevention of Alzheimer's disease. The amyloid peptide Aβ42 has been shown to bind to the α7 nicotinic receptor (Wang et al., J. Biol. Chem., 2000, 275:5626-5632; J. Neurochem. 2000, 75:1155-1161). This association may facilitate the aggregation of Aβ42, believed to be important in the toxic effects of Aβ42, and may also cause disregulation of signaling through α7 nicotinic receptors. Deletion of the α7 receptor gene improves cognitive deficits and synaptic pathology in a mouse model of Alzheimer's disease (Dziewczapolski et al., J. Neuroscience, 2009, pp 8805-8815). The compounds of the present invention may disrupt the interaction of Aβ42 and α7 receptors. Treatment with α7 agonists and partial agonists may represent an approach for disease modification in Alzheimer's disease. Alpha7 receptors may also mediate inflammatory processes in neurodegenerative conditions, such as Alzheimer's disease (Conejero-Goldberg et al., Neurosci. and Biobehav. Rev., 2008, 32, pp 693-706). The α7 agonists and partial agonists of the present invention may be useful in reducing inflammation in neurodegenerative diseases and disorders, such as Alzheimer's disease.

The α7 receptor has also been shown to be involved in the reduction of inflammation via the vagus nerve. In addition, the α7 receptor is expressed in synoviocytes from RA and OA patients, and α7 agonists have been shown to inhibit the proinflammatory cascade that occurs in the rheumatoid joint (Waldberger et al., Arthritis and Rheumatism, Vol 58, pp 3439-3449). Thus, the compounds of the present invention may be useful in the treatment of inflammatory conditions, such as rheumatoid arthritis and osteoarthritis.

Nicotinic receptors containing the α7 subunit are present on mucosal mast cells known to be involved in gastrointestinal hypersensitivity (Kageyama-Yahara et al., Biochem and Biophys. Research Commun., 2008, v. 377, pp 321-325). The α7 agonist GTS-21 inhibits the antigen-induced degranulation of mucosal mast cells, suggesting that α7 agonists may be useful in the treatment of hypersensitive bowel conditions, such as ulcerative colitis.

In a recent report (Marrero et al., JPET Fast Forward, Sep. 28, 2009, DOI: 10.1124/jpet.109.154633), an α7 agonist was shown to decrease weight gain and food intake and reduce the elevated plasma levels of triglycerides, glucose, glycated hemoglobin and TNFa in a mouse model of type II diabetes (db/db mice which are deficit in leptin receptors). The α7 agonists and partial agonists of the present invention may be useful in the treatment of diabetes.

The following references provide general reviews of the nicotinic receptor system and α7 receptors and ligands: Picciotto and Zoli, J. Neurobio. (2002) 53:641-655; Brening, et al, Ann. Reports in Med. Chem. (2005) 40:3-16; Dani and Bertrand, Ann. Rev. Pharm. Tox. (2007) 47:699-729; Olincy and Stevens, Biochem. Pharmacol. (2007) 74:1192-1201; Broad, et al, Drugs Future (2007) 32 (2):161-70; de Jonge and Ulloa, Brit. J. Pharmacol. (2007) 151:915-929; Romanelli, et al, Chem Med Chem (2007) 2(6):746-767; Lightfoot et al., Progress in Medicinal Chemistry (2008), v 46, pp 131-171; Concotta et al., Current Opinion in Investigational Drugs (2008), v 9, pp 47-56; Leiser et al., Pharmacol. and Therapeutics (2009), doi:10:1016/j.pharmthera.2009.03.009).

The invention provides technical advantages, for example, the compounds are novel and are ligands for the nicotinic α7 receptor and may be useful for the treatment of various disorders of the central nervous system, especially affective and neurodegenerative disorders. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds formula I, including Ia and Ib, including pharmaceutically acceptable salts, and compositions and methods of treatment using these compounds. The compounds may be useful for the treatment of various disorders of the central nervous system:

One aspect of the invention is a compound of formula I, or a stereoisomer thereof,

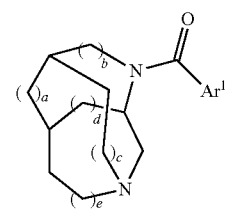

where:
Ar$^1$ is selected from the group consisting of phenyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, pyridinyl, pyridazinyl, pyrimidinyl, pyrazinyl, naphthalenyl, indolyl, indazolyl, benzofuranyl, dihydrobenzofuranyl, benzodioxolanyl, benzothiophenyl, dihydrobenzothiophenyl, benzoisothiazolyl, benzothiazolyl, thienopyrazinyl, pyrrolopyridinyl, pyrrolotriazinyl, benzoisoxazolyl, quinolinyl, isoquinolinyl, quinoxalinyl, and naphthyridinyl, and is substituted with 0-3 substituents selected from the group consisting of cyano, halo, alkyl, haloalkyl, cycloalkyl, alkoxy, haloalkoxy, alkylthio, and Ar$^2$;
Ar$^2$ is phenyl substituted with 0-3 substituents selected from cyano, halo, alkyl, haloalkyl, alkoxy, and haloalkoxy; and
a is 0, b is 1, c is 0, d is 0, and e is 1; or
a is 0, b is 1, c is 1, d is 0, and e is 1; or
a is 1, b is 0, c is 0, d is 1, and e is 0;
or a pharmaceutically acceptable salt thereof.

Another aspect of the invention is a compound of formula I where:
Ar$^1$ is selected from the group consisting of phenyl, furanyl, thienyl, isoxazolyl, isothiazolyl, imidazolyl, thiazolyl, thiadiazolyl, thiazinyl, pyridinyl, pyridazinyl, pyrimidinyl, pyrazinyl, naphthalenyl, indolyl, indazolyl, benzofuranyl, dihydrobenzofuranyl, benzodioxolanyl, benzothiophenyl, dihydrobenzothiophenyl, benzoisothiazolyl, benzothiazolyl, thienopyrazinyl, pyrrolopyridinyl, benzoisoxazolyl, quinolinyl, quinoxalinyl, and naphthyridinyl, and is substituted with 0-2 substituents selected from the group consisting of cyano, halo, alkyl, haloalkyl, cycloalkyl, alkoxy, haloalkoxy, alkylthio, and Ar$^2$; and
Ar$^2$ is phenyl substituted with 0-3 substituents selected from cyano, halo, alkyl, haloalkyl, alkoxy, and haloalkoxy;
or a pharmaceutically acceptable salt thereof.

Another aspect of the invention is a compound of formula I where:
Ar$^1$ is selected from the group consisting of phenyl, furanyl, thienyl, isoxazolyl, isothiazolyl, imidazolyl, thiazolyl, thiadiazolyl, thiazinyl, triazinyl, pyridinyl, pyridazinyl, pyrimidinyl, pyrazinyl, naphthalenyl, indolyl, indazolyl, benzofuranyl, dihydrobenzofuranyl, benzodioxolanyl, benzothiophenyl, dihydrobenzothiophenyl, benzoisothiazolyl, benzothiazolyl, thienopyrazinyl, pyrrolopyridinyl, benzoisoxazolyl, quinolinyl, quinoxalinyl, and naphthyridinyl, and is substituted with 0-2 substituents selected from the group consisting of halo, alkyl, haloalkyl, alkoxy, alkylthio, and $Ar^2$; and $Ar^2$ is phenyl substituted with 0-1 halo;
or a pharmaceutically acceptable salt thereof.

Another aspect of the invention is a compound of formula I where a is 0, b is 1, c is 0, d is 0, and e is 1.

Another aspect of the invention is a compound of formula I where a is 0, b is 1, c is 1, d is 0, and e is 1.

Another aspect of the invention is a compound of formula I where a is 1, b is 0, c is 0, d is 1, and e is O.

Another aspect of the invention is a compound of formula I where $Ar^1$ is indazolyl substituted with 0-3 substituents selected from the group consisting of cyano, halo, alkyl, haloalkyl, cycloalkyl, alkoxy, and haloalkoxy; or a pharmaceutically acceptable salt thereof.

For a compound of formula I, the scope of any instance of a variable substituent, including $Ar^1$, $Ar^2$, a, b, c, d, and e, can be used independently with the scope of any other instance of a variable substituent. As such, the invention includes combinations of the different aspects.

Unless specified otherwise, these terms have the following meanings. "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic (for example, naphthyl) or non-aromatic (for example, indanyl, indenyl, tetrahydronaphthyl) carbocyclic ring. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Some of the compounds may be prepared using the reactions and techniques described in this section. The reactions are performed in solvents appropriate to the reagents and materials employed and are suitable for the transformations being effected. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "$Et_2O$" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3 SO_2—$; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Scheme 1.

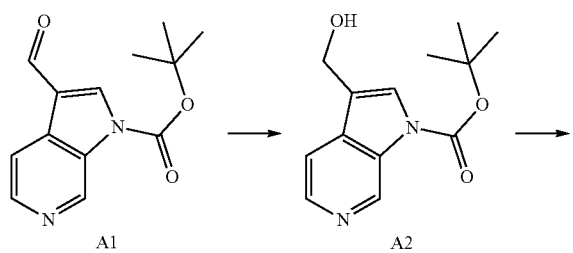

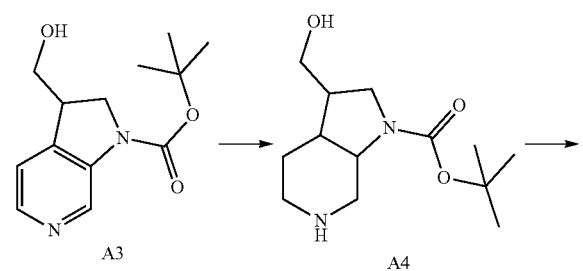

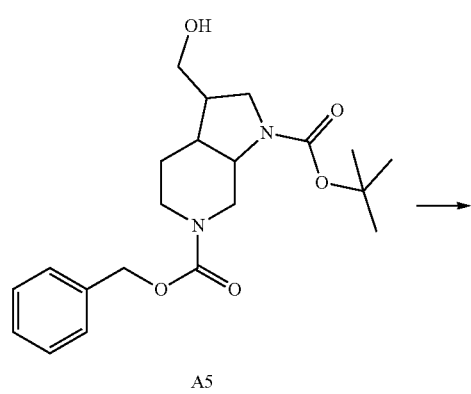

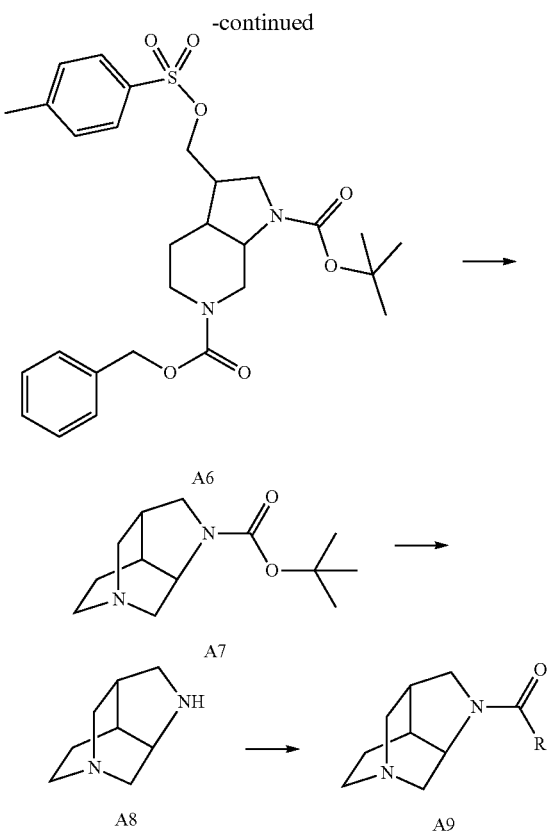

Compounds of Formula I can be prepared as illustrated in Reaction Scheme 1. The aldehyde of Formula A1 is known and may be prepared by methods known to those skilled in the art. Reduction of the aldehyde to the corresponding alcohol A2 may be performed by the use of a reducing agent, for example sodium borohydride. Reduction of the azaindole to the azaindoline A3 may be accomplished by hydrogenation over a suitable catalyst, for example palladium hydroxide. Further reduction to piperidine A4 may be performed by hydrogenation over a suitable catalyst, for example platinum oxide. Protection of the piperidine may be accomplished by treatment with benzyl chloroformate. Carbamate A5 may be converted to the corresponding tosylate A6 by treatment with tosyl chloride in the presence of pyridine. Cleavage of the benzyl carbamate may be accomplished by hydrogenation over a suitable catalyst, for example palladium on carbon, followed by treatment with base and warming to afford tricycle A7.

Cleavage of the Boc group found in tricycle A7, affording amine A8, can be performed by methods known to those skilled in the art, for example, treatment with trifluoroacetic acid or hydrogen chloride. Conversion of A8 to compounds of Formula 1 can be performed by a variety of methods known to those skilled in the art, for example by treatment with the appropriate carboxylic acid, an amide coupling reagent such as HATU or EDC and an amine base such as triethylamine or diisopropylethylamine.

Scheme 2.

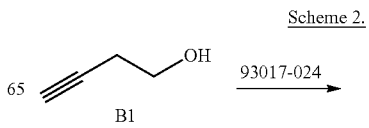

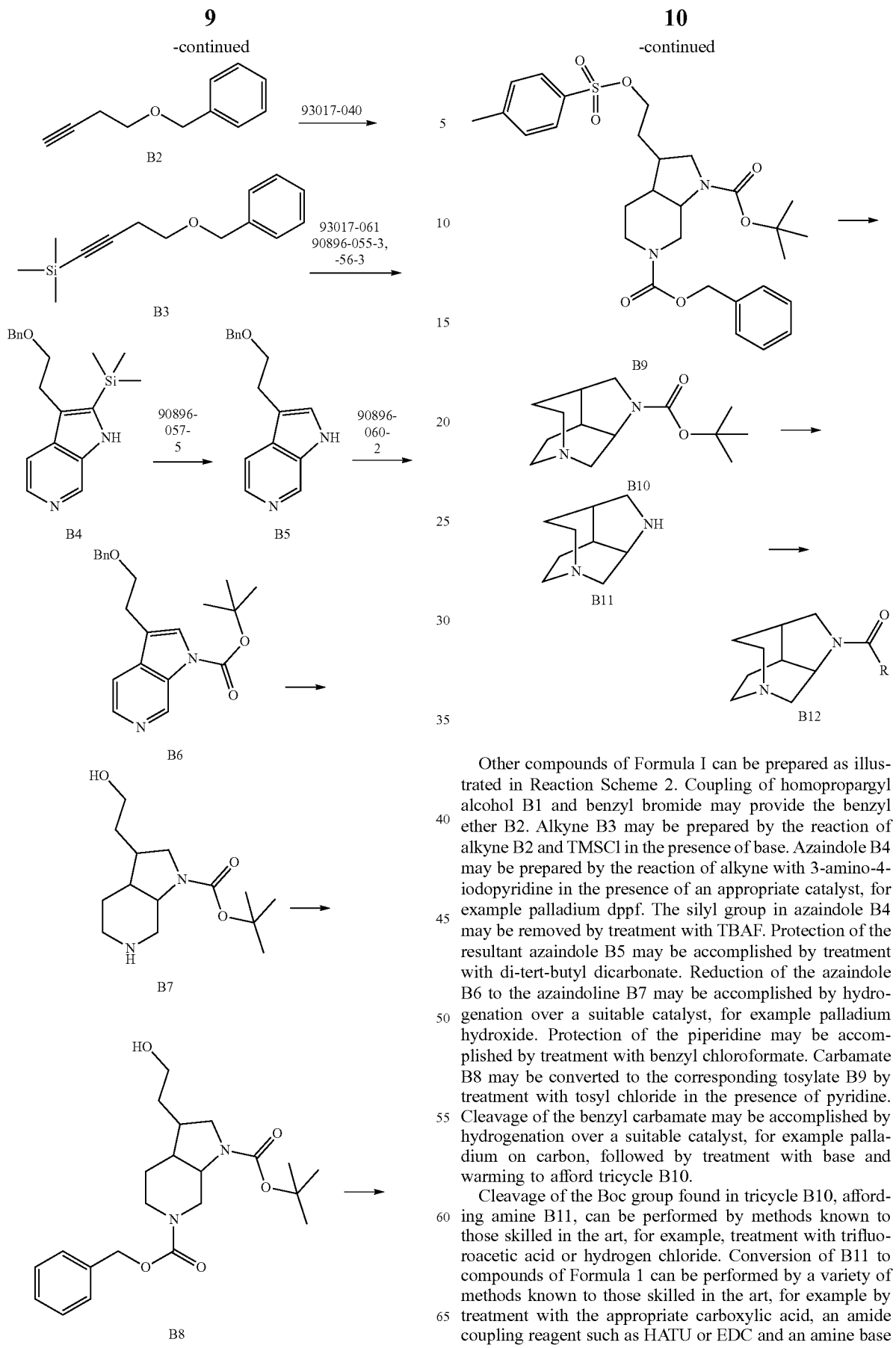

Other compounds of Formula I can be prepared as illustrated in Reaction Scheme 2. Coupling of homopropargyl alcohol B1 and benzyl bromide may provide the benzyl ether B2. Alkyne B3 may be prepared by the reaction of alkyne B2 and TMSCl in the presence of base. Azaindole B4 may be prepared by the reaction of alkyne with 3-amino-4-iodopyridine in the presence of an appropriate catalyst, for example palladium dppf. The silyl group in azaindole B4 may be removed by treatment with TBAF. Protection of the resultant azaindole B5 may be accomplished by treatment with di-tert-butyl dicarbonate. Reduction of the azaindole B6 to the azaindoline B7 may be accomplished by hydrogenation over a suitable catalyst, for example palladium hydroxide. Protection of the piperidine may be accomplished by treatment with benzyl chloroformate. Carbamate B8 may be converted to the corresponding tosylate B9 by treatment with tosyl chloride in the presence of pyridine. Cleavage of the benzyl carbamate may be accomplished by hydrogenation over a suitable catalyst, for example palladium on carbon, followed by treatment with base and warming to afford tricycle B10.

Cleavage of the Boc group found in tricycle B10, affording amine B11, can be performed by methods known to those skilled in the art, for example, treatment with trifluoroacetic acid or hydrogen chloride. Conversion of B11 to compounds of Formula 1 can be performed by a variety of methods known to those skilled in the art, for example by treatment with the appropriate carboxylic acid, an amide coupling reagent such as HATU or EDC and an amine base such as triethylamine or diisopropylethylamine.

Scheme 3.

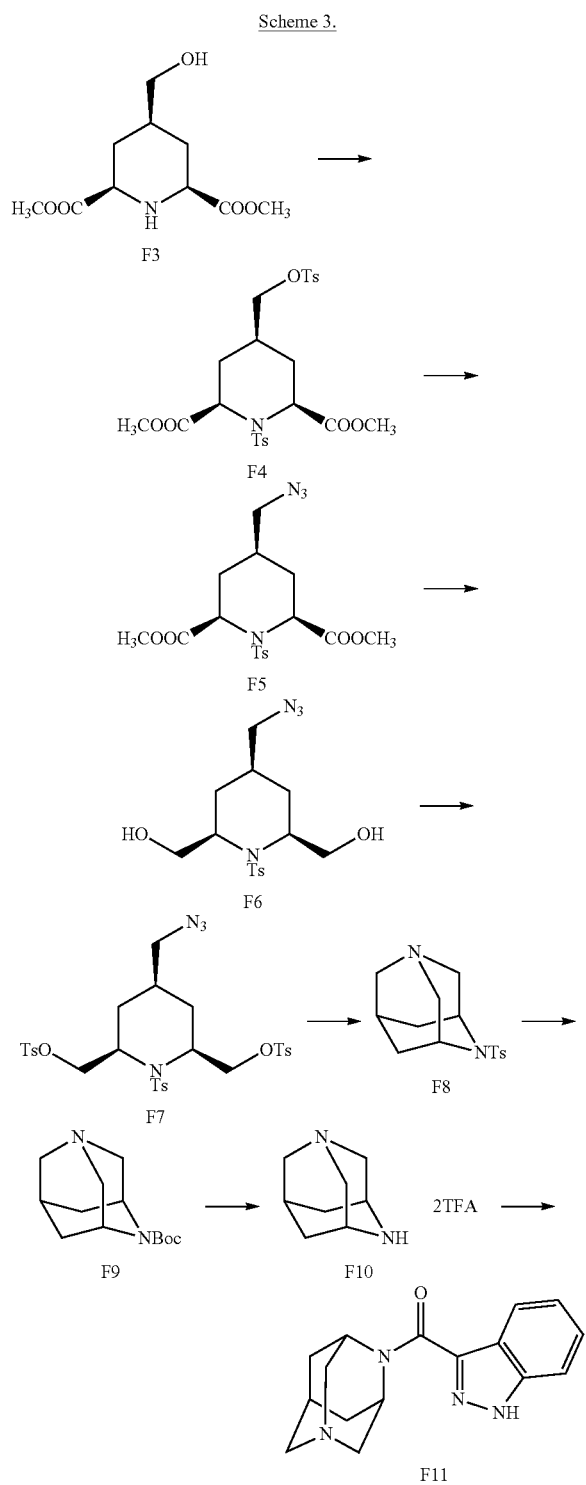

Additional compounds of Formula I can be prepared as illustrated in Reaction Scheme 3. The piperidine of Formula F3 is known and may be prepared by methods known to those skilled in the art. Piperidine F3 may be converted to its bis-tosylate by reaction with reagents such as tosyl chloride and a base such as pyridine. Displacement of the tosylate leaving group may be performed by treatment with a nucleophilic azide source such as sodium azide. Selective reduction of the esters in compound F5 may be accomplished using a reducing agent such as lithium borohydride to afford diol F6. The alcohols present in F6 may be converted to good leaving groups, such as tosylates, by treatment with reagents such as tosyl chloride and a base such as pyridine. Reduction of the azide with concomitant cyclization may be facilitated by reduction with a tertiary phosphine, such as trimethylphosphine. Conversion of the tosamide protecting group to a Boc protecting group may be carried out using a dissolving metal reduction, such as lithium naphthalenide followed by treatment with Boc anhydride.

Cleavage of the Boc group found in tricycle F9, affording amine F10, can be performed by methods known to those skilled in the art, for example, treatment with trifluoroacetic acid or hydrogen chloride. Conversion of F10 to compounds of Formula 1 can be performed by a variety of methods known to those skilled in the art, for example by treatment with the appropriate carboxylic acid, an amide coupling reagent such as HATU or EDC and an amine base such as triethylamine or diisopropylethylamine.

Biological Methods

I) α7 Nicotinic Acetylcholine Receptor Binding.

Membranes were prepared for binding using HEK293 cells stably expressing the rat α7 nicotinic acetylcholine receptor (rat α7 nAChR). Cells were homogenized at 4° C. in hypotonic lysis buffer consisting of 10 mM Tris (pH 7.4), 5 mM EDTA and protease inhibitors and centrifuged at 32000×g for 20 minutes. The pellet was washed once in membrane wash buffer consisting of 50 mM Tris (pH 7.4), 1 mM EDTA and protease inhibitors and centrifuged at 32000×g for 20 minutes. This pellet was then resuspended in assay buffer consisting 50 mM $KH_2PO_4$ (pH 7.4 at 25° C.), 1 mM EDTA, 0.005% Triton-X 100 and 0.1% (v/v) Sigma Protease Inhibitor Cocktail. Aliquots were then frozen in dry ice/ethanol and kept at −80° C. until the day of the assay.

II) A $Ca^{2+}$-Sensitive, Fluorescence-Based Assay α-7 for Nicotinic Acetylcholine Receptor Channel Function in Mammalian Cells ("FLIPR"). Summary:

Lead compounds are evaluated for agonist activity at α-7, α3β4, α4αβ2, and α1β1δ1ε sub-types of nicotinic ACh receptor ion channels expressed in mammalian HEK 293 cells. Agonist potency and efficacy values are determined from kinetic fluorescence $Ca^{2+}$ influx measurements made using a 384 well FLIPR (Fluorescence Image Plate Reader). The utility of fluorescent indicators for measuring changes in intracellular divalent cation concentrations, particularly $Ca^{2+}$, for drug discovery endeavors is well documented (Rudiger, R., et al., *Nature Reviews,* 2003, 4:579-586; Gonzalez J. E., et al., *Receptors and Channels,* 2002, 8:283-295). In this assay, channel expressing HEK cell lines seeded in 384 well assay plates are loaded with a membrane permeant fluorescent $Ca^{2+}$ indicator dye, whose 510 nm green emission signal increases in response to elevation of intracellular $Ca^{2+}$ concentration. The basal fluorescence from the cells is monitored in real time, followed by the acute addition of test compounds. If the compound is an agonist at any of the non-selective cation channels, the latter open and allow the movement of extracellular $Ca^{2+}$ ions into the cell cytoplasm, where they bind to the $Ca^{2+}$ indicator dye, and produce an increase in fluorescence output signal, which is detected by a cooled CCD imaging camera.

Materials and Methods:

Reagents: The acetomethoxy (AM) ester of the $Ca^{2+}$ indicator dye Fluo-4 was obtained from InVitrogen, (Carlsbad, Calif.). Acetylcholine and all buffer constituents were purchased from Sigma Chemical Company, St. Louis, Mo.

G418 and Minimal Essential Medium were purchased from InVitrogen Life Technologies, Carlsbad, Calif. Fetal bovine serum was purchased from (InVitrogen, Carlsbad, Calif.).

Cell Culture:

HEK-293 cells were grown in Minimal Essential Medium containing 10% (v/v) fetal bovine serum at 37° C. in a 5% $CO_2$ incubator. HEK-293 cells stably expressing the ion channels were grown in the same medium with the addition of 500 μg/ml G418.

$Ca^{2+}$ Flux Assays of $Ca^{2+}$ Channels Expressed in HEK-293 Cells:

HEK-293 cells expressing the ion channels of interest were plated in 384 well, black-walled, clear-bottomed, poly-D-lysine coated plates at a density of ~20,000 cells/well in 20 μl of Minimal Essential Medium containing 10% (v/v) fetal bovine serum and incubated for 2 days at 29° C. in a 5% $CO_2$ incubator. Prior to assay, cells were loaded with the Fluo-4 AM ester. Cell loading was accomplished by removing the culture medium and replacing it with 30 μl/well of the AM ester of the dye (5 μM) mixed with Hanks Balanced Salt Solution (#14175-095) containing 20 mM HEPES, 2.5 mM probenecid, 0.5 mM $CaCl_2$, 1 mM MgCl2 and 10 μM atropine. Dye loading was allowed to proceed for 90 minutes at room temperature at which time the dye loading solution was removed and replaced with 40 μl/well of Hanks buffer. Cells loaded with dye were loaded onto a FLIPR384 (Molecular Devices, Sunnyvale, Calif.). Fluo-4 dye was excited using the 488 nm line of an argon laser. Emission was filtered using a 540+/−30 nm bandpass filter. For evaluation of the effects of test compounds using the $Ca^{2+}$ flux assay, compounds to be tested were provided in assay ready plates. For nicotinic receptor ion channel expressing cells, the assay was initiated by the addition of 20 μl/well of Hanks buffer containing test compounds. For all assays, data were collected at 1 Hz for 10 seconds (baseline), at which time the compound containing stimulus buffers are added, and further measurements collected at 0.33 Hz for 3 min.

Data Analysis:

The statistical robustness of the nicotinic receptor $Ca^{2+}$ flux assays is determined from blanks and totals wells. The totals wells define maximal channel activation for each compound test plate (Maximum efficacious dose of acetylcholine), and the blanks wells which contain matched DMSO only, define zero channel activation. The raw fluorescence units data files generated on the FLIPR plate reader are automatically exported and processed by in-house data analysis tools. The reduced percent activation data for each concentration of test compound are fit using MathIQ fitting engine (ID Business Solutions Limited, Surrey, UK). Data were analyzed by fitting maximum amplitudes of change in fluorescence, for $Ca^{2+}$ flux for a given condition of test compound. Potencies ($EC_{50}$ values) of compounds are calculated from the average of three assay wells from a twenty point CRC. Test compound efficacy values (Ymax values) are expressed relative to a maximal response to acetylcholine in the total wells.

III) Fos Quantification Assay:

Male Wistar rats are treated with drug (1-10 mg/kg) or vehicle (2 ml/kg, sc). Two hours after treatments, the rats are rapidly decapitated and discrete brain regions of interest are isolated on ice and weighed and flash frozen with liquid nitrogen and stored at −80 deg. C. Further processing of the brain tissue for nuclear extracts as well as for Fos quantification are in accordance with the protocol prescribed by a commercially available ELISA-based chemiluminiscence detection kit (catalog #89860, EZ-detect c-Fos Trans kit, Pierce Biotechnology Inc., Rockford, Ill.).

IV) MK-801 Disrupted Set-Shift Assay in Rats:

This assay uses a modification of the protocol described by Stefani et al. (*Behavioral Neuroscience*, 2003, 117: 728-737). Test compounds are assessed for their ability to reverse an MK-801-induced performance deficit (0.03 mg/kg, i.p., single dose) in this assay.

The activity of specific compounds described herein and tested in the above assay (II) is provided in Table 1.

TABLE 1

Core structure: diazatricyclic amine N-acylated with C(=O)R

| Example Number | R | FLIPR α7 ($EC_{50}$, nM) |
|---|---|---|
| 1 | 7-chlorobenzothiophen-2-yl | 1700 |
| 2 | 1H-indazol-3-yl | 250 |
| 3 | phenyl | >100000 |
| 4 | 2-methoxyphenyl | >100000 |
| 5 | 4-chlorophenyl | >100000 |
| 6 | furan-2-yl | >100000 |

TABLE 1-continued
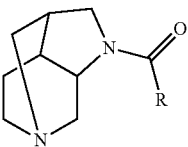
| Example Number | R | FLIPR α7 (EC$_{50}$, nM) |
|---|---|---|
| 7 | 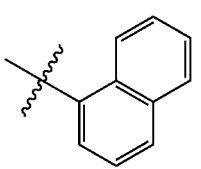 [SMILES: *c1cccc2ccccc12] | >100000 |
| 8 | 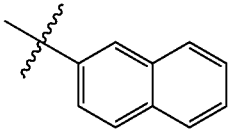 [SMILES: *c1ccc2ccccc2c1] | >100000 |
| 9 | 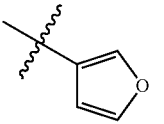 [SMILES: *c1ccoc1] | NT |
| 10 | 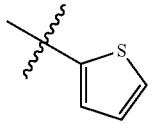 [SMILES: *c1cccs1] | NT |
| 11 | 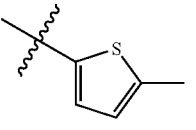 [SMILES: *c1ccc(C)s1] | >100000 |
| 12 | 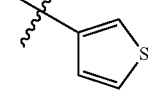 | 6600 |
| 13 | 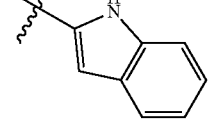 | >100000 |
| 14 | 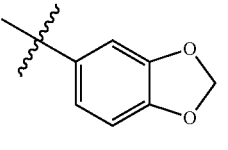 [SMILES: *c1ccc2c(c1)OCO2] | >100000 |
| 15 | 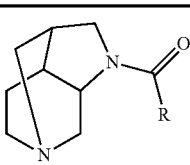 | >100000 |
| 16 | 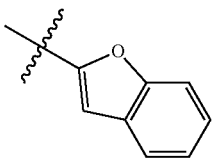 [SMILES: *c1cc2ccccc2o1] | 4500 |
| 17 | | >100000 |
| 18 | | >100000 |
| 19 | | NT |
| 20 | | 18000 |
| 21 | | >100000 |
| 22 | | >100000 |
| 23 | | >100000 |

TABLE 1-continued
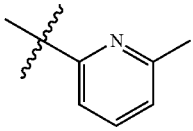 [SMILES: *c1cccc(C)n1]
| Example Number | R | FLIPR α7 (EC$_{50}$, nM) |
|---|---|---|
| 24 | 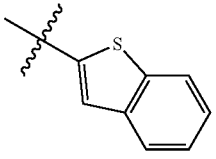 [SMILES: *c1cc2ccccc2s1] | >100000 |
| 25 | 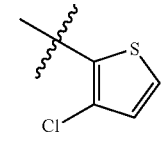 [SMILES: *c1sccc1Cl] | 590 |
| 26 | 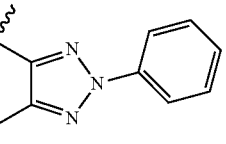 | >100000 |
| 27 | 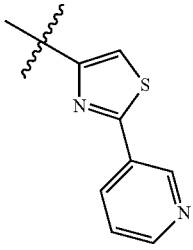 [SMILES: *c1csc(-c2cccnc2)n1] | >100000 |
| 28 | 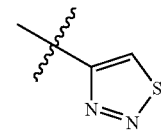 [SMILES: *c1csnn1] | >100000 |
| 29 | 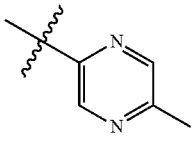 [SMILES: *c1cnc(C)cn1] | >100000 |
| 30 | 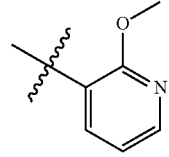 [SMILES: *c1cccnc1OC] | 3900 |
| 31 | 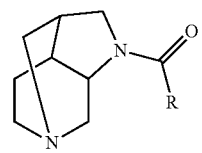 | >100000 |
TABLE 1-continued
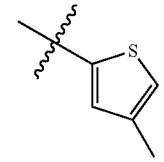 [SMILES: *c1cc(C)cs1]
| Example Number | R | FLIPR α7 (EC$_{50}$, nM) |
|---|---|---|
| 32 | 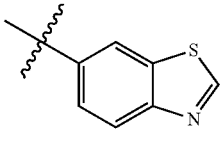 [SMILES: *c1ccc2ncsc2c1] | >100000 |
| 33 | 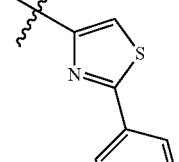 | >100000 |
| 34 | 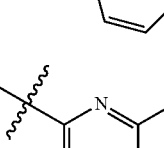 | >100000 |
| 35 | 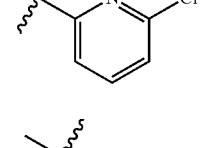 | >100000 |
| 36 | 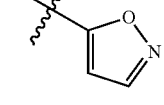 | >100000 |
| 37 | 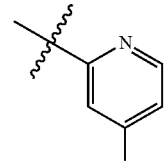 | >100000 |
| 38 | 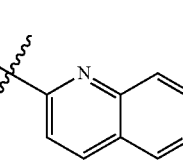 | >100000 |
| 39 | 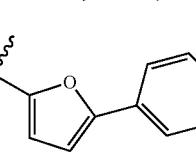 | >100000 |

TABLE 1-continued

| Example Number | R | FLIPR α7 (EC$_{50}$, nM) |
|---|---|---|
| 40 | thiazol-5-yl | >100000 |
| 41 | 2,3-dihydrobenzofuran-7-yl | >100000 |
| 42 | pyrimidin-5-yl | >100000 |
| 43 | 5-methylisoxazol-3-yl | >100000 |
| 44 | 1-methylindol-3-yl | >100000 |
| 45 | quinoxalin-6-yl | 25000 |
| 46 | 1-methylimidazol-2-yl | >100000 |
| 47 | benzothiazol-2-yl | >100000 |
| 48 | pyridin-4-yl | >100000 |
| 49 | quinolin-2-yl | >100000 |
| 50 | 5-bromo-1H-indazol-3-yl | >100000 |
| 51 | 3,4-dibromothiophen-2-yl | >100000 |
| 52 | 3-chloro-6-fluorobenzothiophen-2-yl | >100000 |
| 53 | 1-methylindazol-3-yl | >100000 |
| 54 | 2-methylindazol-3-yl | >100000 |
| 55 | 1H-pyrrolo[2,3-b]pyridin-3-yl | >100000 |

TABLE 1-continued

| Example Number | R | FLIPR α7 (EC$_{50}$, nM) |
|---|---|---|
| 56 | 3-bromoisoxazol-5-yl | >100000 |
| 57 | 4,5-dibromofuran-2-yl | >100000 |
| 58 | 3-isopropylisoxazol-5-yl | >100000 |
| 59 | 4-bromothiophen-2-yl | >100000 |
| 60 | 5-bromo-7-methoxybenzofuran-2-yl | >100000 |
| 61 | 6-methoxy-1H-indazol-3-yl | 1100 |
| 62 | 3-phenylisoxazol-5-yl | >100000 |
| 63 | 5-chloro-1H-indazol-3-yl | 400 |
| 64 | 3-methylisoxazol-5-yl | >100000 |
| 65 | 4-bromo-3-methylthiophen-2-yl | >100000 |
| 66 | 4-phenylthiophen-2-yl | >100000 |
| 67 | 3-chlorobenzo[b]thiophen-2-yl | >100000 |
| 68 | 3-chloro-6-methylbenzo[b]thiophen-2-yl | >100000 |
| 69 | 4-(4-bromophenyl)thiophen-2-yl | >100000 |

TABLE 1-continued

| Example Number | R | FLIPR α7 (EC$_{50}$, nM) |
|---|---|---|
| 70 | 2,5-dimethylfuran | >100000 |
| 71 | 6-chlorobenzothiophen-2-yl | >100000 |
| 72 | 4-trifluoromethylbenzothiophen-2-yl | >100000 |
| 73 | 5-bromobenzothiophen-2-yl | >100000 |
| 74 | 4-chlorobenzothiophen-2-yl | >100000 |
| 75 | thieno[3,2-b]pyrazin-6-yl | >100000 |
| 76 | 3,4-dichloroisothiazol-5-yl | >100000 |
| 77 | 4-methoxy-1H-indazol-3-yl | 22000 |
| 78 | isothiazol-5-yl | >100000 |
| 79 | 3,4-dichlorobenzothiophen-2-yl | >100000 |
| 80 | 5-bromo-7-azaindol-3-yl | 38000 |
| 81 | benzo[d]isoxazol-3-yl | 8000 |
| 82 | benzo[c]isoxazol-3-yl | >100000 |
| 83 | 3-methylthio-4,5,6,7-tetrahydrobenzo[c]isothiazol-3-yl | >100000 |

TABLE 1-continued

| Example Number | R | FLIPR α7 (EC$_{50}$, nM) |
|---|---|---|
| 84 | 4-(4-chlorophenyl)thiophen-2-yl | >100000 |
| 85 | 3-chloro-4-fluorobenzo[b]thiophen-2-yl | >100000 |
| 86 | 5-chloro-3-methylbenzo[b]thiophen-2-yl | >100000 |

TABLE 2

| Example Number | R | FLIPR α7 (EC$_{50}$, nM) |
|---|---|---|
| 88 | 1H-indazol-3-yl | 390 |
| 89 | benzo[b]thiophen-2-yl | 18000 |
| 90 | 1-methyl-1H-indazol-3-yl | >100000 |
| 91 | 1-methyl-1H-indol-3-yl | >100000 |
| 92 | 5-chloro-1H-indazol-3-yl | 700 |
| 93 | 6-methoxy-1H-indazol-3-yl | 2200 |
| 94 | 4-chlorobenzo[b]thiophen-2-yl | >100000 |
| 95 | 4-methoxy-1H-indazol-3-yl | >100000 |
| 96 | 7-chlorobenzo[b]thiophen-2-yl | >100000 |

TABLE 2-continued

[Structure: bicyclic amine with N-C(=O)-R substituent]

| Example Number | R | FLIPR α7 (EC$_{50}$, nM) |
|---|---|---|
| 97 | 1,2-benzisothiazol-3-yl | 30000 |
| 98 | 4-chlorophenyl | >100000 |
| 99 | benzofuran-2-yl | 35000 |

TABLE 3

[Structure: bicyclic amine with N-C(=O)-R substituent]

| Example Number | R | FLIPR α7 (EC$_{50}$, nM) |
|---|---|---|
| 87 | 1H-indazol-3-yl | 370 |
| 100 | benzothiophen-2-yl | 11000 |
| 101 | 1-methyl-1H-indazol-3-yl | >100000 |
| 102 | 1-methyl-1H-indol-3-yl | >100000 |
| 103 | 5-chloro-1H-indazol-3-yl | >100000 |
| 104 | 6-methoxy-1H-indazol-3-yl | >100000 |
| 105 | 5-bromo-1H-indazol-3-yl | >100000 |
| 106 | 4-chlorobenzothiophen-2-yl | >100000 |
| 107 | 4-methoxy-1H-indazol-3-yl | 30000 |

TABLE 3-continued

| Example Number | R | FLIPR α7 (EC$_{50}$, nM) |
|---|---|---|
| 108 | 7-chloro-benzothiophen-2-yl | >100000 |
| 109 | 6-chloro-1H-indazol-3-yl | >100000 |
| 110 | 5-methoxy-1H-indazol-3-yl | >100000 |
| 111 | benzo[d]isothiazol-3-yl | 36000 |
| 112 | 4-chlorophenyl | >100000 |
| 113 | benzofuran-2-yl | >100000 |

TABLE 4

| Example Number | R | FLIPR α7 (EC$_{50}$, nM) |
|---|---|---|
| 114 | 1H-indazol-3-yl | 470 |

TABLE 5

| Example Number | R | FLIPR α7 (EC$_{50}$, nM) |
|---|---|---|
| 115 | 1H-indazol-3-yl | 73 |

Pharmaceutical Compositions and Methods of Treatment

Compounds of formula I bind to the alpha7 nicotinic acetylcholine receptor and can be useful in treating affective disorders and neurodegenerative disorders. Therefore, another aspect of the invention is a composition comprising a compound of formula I, or a pharmaceutically acceptable salt thereof, and a pharmaceutically acceptable carrier.

Another aspect of the invention is the use of a compound of formula I in the manufacture of a medicament for the treatment of affective disorders or neurodegenerative disorders.

Another aspect of the invention is the use of a compound of formula I in the manufacture of a medicament for the treatment of schizophrenia or Alzheimer's Disease.

Another aspect of the invention is a method of treating affective disorders or neurodegenerative disorders comprising administering to a patient a therapeutically effective amount of a compound of formula I.

Another aspect of the invention is a method of treating schizophrenia or Alzheimer's Disease comprising administering to a patient a therapeutically effective amount of a compound of formula I.

Another aspect of the invention is a method of treating schizophrenia comprising administering to a patient a therapeutically effective amount of a compound of formula I.

Another aspect of the invention is a method of treating Alzheimer's Disease comprising administering to a patient a therapeutically effective amount of a compound of formula I.

Another aspect of the invention is a method of treating cognitive disorders comprising administering to a patient a therapeutically effective amount of a compound of formula I.

Another aspect of the invention is a method of treating rheumatoid arthritis comprising administering to a patient a therapeutically effective amount of a compound of formula I.

Another aspect of the invention is a method of treating osteoarthritis comprising administering to a patient a therapeutically effective amount of a compound of formula I.

Another aspect of the invention is a method of treating ulcerative colitis comprising administering to a patient a therapeutically effective amount of a compound of formula I.

Another aspect of the invention is a method of treating Crohn's Disease comprising administering to a patient a therapeutically effective amount of a compound of formula I.

Another aspect of the invention is a method of treating diabetes comprising administering to a patient a therapeutically effective amount of a compound of formula I.

"Patient" means a person suitable for therapy as understood by practitioners in the field of affective disorders and neurodegenerative disorders.

"Treatment," "therapy," and related terms are used as understood by practitioners in the field of affective disorders and neurodegenerative disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred.

Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS $^1$H-NMR spectra were run on a Bruker 600, 500, or 400 MHz instrument and chemical shifts were reported in ppm ($\delta$) with reference to tetramethylsilane ($\delta$=0.0). All evaporations were carried out under reduced pressure.

LC/MS Analysis Methods:

LC/MS analysis Method A: Phenomenex-Luna 50×2.0 mm 3.0 um column employing a flow rate of 0.8 mL/min with solvent A=9:1 Water/Methanol+0.1% TFA and solvent B=1:9 Water/Methanol+0.1% TFA. A gradient elution [0-100% in 4 min, with a 5 min run time] and a UV detector set at 220 nm.

LC/MS analysis Method B: Phenomenex-Luna 50×2.0 mm 3.0 um column employing a flow rate of 0.8 mL/min with Mobile Phase A: 5:95 methanol:water with 10 mM ammonium acetate; Mobile Phase B: 95:5 methanol:water with 10 mM ammonium acetate; Temperature: 40° C.; A gradient elution [0-100% in 4 min, with a 5 min run time] Flow: 0.8 mL/min. and a UV detector set at 220 nm.

EXAMPLE 1

(7-chlorobenzo[b]thiophen-2-yl)(hexahydro-3,6-methanopyrrolo[2,3-c]pyridin-1(2H)-yl)methanone

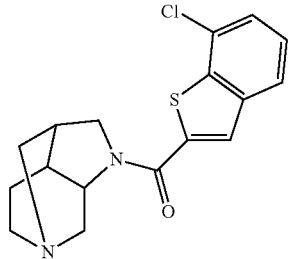 [SMILES: O=C(c1cc2cccc(Cl)c2s1)N1CC2CN3CCC2C1C3]

Step A: (tert-butyl 3-(hydroxymethyl)-1H-pyrrolo[2,3-c]pyridine-1-carboxylate

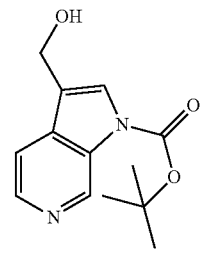 [SMILES: CC(C)(C)OC(=O)n1cc(CO)c2ccncc21]

Tert-butyl 3-formyl-1H-pyrrolo[2,3-c]pyridine-1-carboxylate (2.5 g, 10.15 mmol) was dissolved in MeOH (75 mL) and sodium borohydride was added (0.155 g, 4.1 mmol). The mixture was stirred for 10 min, at which point TLC analysis showed the starting material to have been consumed, so the mixture was carefully quenched by the addition of 1N HCl (~2 mL), diluted with water and extracted with chloroform thrice. The organics were dried over sodium sulfate, filtered and evaporated to afford (tert-butyl 3-(hydroxymethyl)-1H-pyrrolo[2,3-c]pyridine-1-carboxylate (2.5 g, 99% yield) which was used directly in the next step without further purification or analysis.

Alternate procedure: The following alternate procedure was also employed which used a different work-up of the reaction: tert-butyl 3-formyl-1H-pyrrolo[2,3-c]pyridine-1-carboxylate (8.94 g, 36.3 mmol) was dissolved in MeOH (250 mL) and sodium borohydride was added (0.55 g, 14.5 mmol). The mixture was stirred for 10 min, at which point TLC analysis showed the starting material to have been consumed, so the mixture was carefully quenched by the addition of 1N HCl (~2 mL) and the solvent was evaporated. The residue was partitioned between with 1N HCl and chloroform. The phases were separated and the aqueous was washed twice with chloroform, the combined chloroform washes were re-extracted with 1N HCl and the combined aqueous fractions were made basic by the addition of 10N NaOH. The basic aqueous fraction was extracted with chloroform thrice. These organic extracts were dried over sodium sulfate, filtered and evaporated to afford (tert-butyl 3-(hydroxymethyl)-1H-pyrrolo[2,3-c]pyridine-1-carboxylate (8.8 g, 98% yield) which was used directly in the next step without further purification. $^1$H NMR (400 MHz, CHLOROFORM-d) δ=9.37 (s, 1H), 8.40 (d, J=5.3 Hz, 1H), 7.73 (s, 1H), 7.59 (dd, J=1.1, 5.4 Hz, 1H), 4.87 (s, 2H), 2.72 (br. s, 1H), 1.70 (s, 9H).

Step B: 6-benzyl 1-tert-butyl 3-((tosyloxy)methyl) hexahydro-1H-pyrrolo[2,3-c]pyridine-1,6(2H)-dicarboxylate

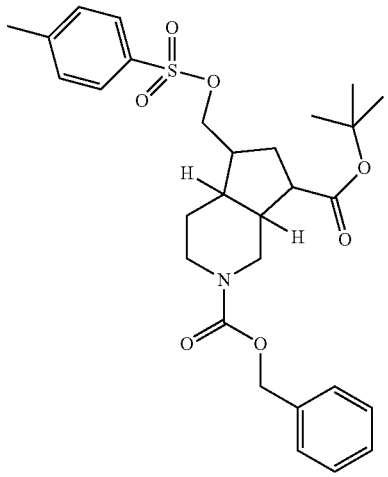

A solution of (tert-butyl 3-(hydroxymethyl)-1H-pyrrolo[2,3-c]pyridine-1-carboxylate (2.5 g, 10 mmol) in ethanol (250 mL) was passed through a H-Cube flow hydrogenator over a Pd(OH)2 cartridge at 1 mL/min, 20° C. and 70 bar. Although the initial portion to elute from the reactor was mostly reduced product by TLC, the reaction became less effective over time. The temperature was raised to 40° C., but the final material was only ~3:1 product: starting material, so the whole amount was taken forward, evaporated to ~100 mL volume and added to a Parr bottle containing 10% palladium hydroxide (0.6 g). The mixture was hydrogenated at 55 psi overnight, filtered through celite and concentrated to ~80 mL volume. To this was added acetic acid (20 mL) and platinum oxide (550 mg, 2.4 mmol). The mixture was hydrogenated on a Parr apparatus at 55 psi overnight, filtered through celite and evaporated to give a yellow oil. This yellow oil was resuspended in THF (50 mL) and 10% aq. potassium carbonate (50 mL) and to this, CBZ-Cl was added (1.5 mL, 10.5 mmol). The mixture was stirred vigorously for 30 min, poured into 200 mL chloroform, the layers separated and the aqueous fraction extracted again with chloroform. The combined organics were washed with brine, dried over sodium sulfate, filtered and evaporated. The residue was redissolved in pyridine (25 mL), cooled on an ice bath and TsCl (2 g, 10.5 mmol) was added. The mixture was allowed to warm to ambient temperature and stirred overnight. The mixture was diluted with toluene and the bulk of the solvent was removed on the rotovap, then partitioned between ethyl acetate and 0.5M HCl (300 mL). The phases were separated and the organics were washed once more with brine, dried over sodium sulfate, filtered and evaporated. The residue was purified by silica gel chromatography (20-50% EtOAc/Hex) to afford 6-benzyl 1-tert-butyl 3-((tosyloxy)methyl) hexahydro-1H-pyrrolo[2,3-c]pyridine-1,6(2H)-dicarboxylate (3.7 g, 67% yield). LCMS method A: retention time=4.11 min, M+H-Boc=445.2. $^1$H NMR (400 MHz, CHLOROFORM-d) δ=7.80 (d, J=8.3 Hz, 2H), 7.48-7.31 (m, 7H), 5.43-4.84 (m, 2H), 4.48-2.87 (m, 9H), 2.66-2.35 (m, 5H), 1.70-1.36 (m, 11H) (HNMR complicated by diastereomixture and rotomers).

Alternate procedure: The following alternate procedures were also employed which isolated and characterized some of the intermediates:

Step B1: tert-butyl 3-(hydroxymethyl)-2,3-dihydro-1H-pyrrolo[2,3-c]pyridine-1-carboxylate

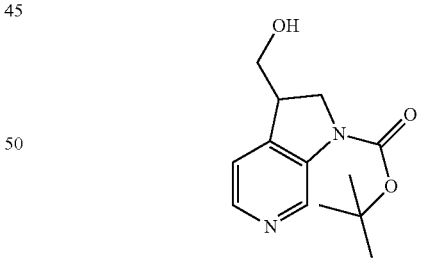

A solution of tert-butyl 3-(hydroxymethyl)-1H-pyrrolo[2,3-c]pyridine-1-carboxylate (8.9 g, 35.8 mmol) in ethanol (Volume: 300 mL) was added to a Parr bottle containing 10% palladium hydroxide on carbon (2 g, 1.424 mmol) and the mixture was hydrogenated at 55 psi overnight, flushed with nitrogen, filtered through celite and evaporated to afford tert-butyl 3-(hydroxymethyl)-2,3-dihydro-1H-pyrrolo[2,3-c]pyridine-1-carboxylate (8.96 g, 35.8 mmol, 100% yield), which was used in the next step without further purification. LCMS method A: retention time=2.84 min, M+H=251.2.

Step B2: tert-butyl 3-(hydroxymethyl)octahydro-1H-pyrrolo[2,3-c]pyridine-1-carboxylate, AcOH

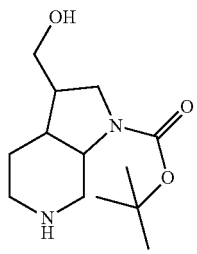 [SMILES: CC(C)(C)OC(=O)N1CC(CO)C2CCNCC21]

A solution of tert-butyl 3-(hydroxymethyl)-2,3-dihydro-1H-pyrrolo[2,3-c]pyridine-1-carboxylate (8.96 g, 35.8 mmol, 35.8 mmol) in ethanol (130 mL) and acetic acid (20 mL) was added to a Parr bottle containing platinum oxide (1.5 g, 6.6 mmol). The mixture was hydrogenated at 55 psi for 3d, then filtered through celite and evaporated to give tert-butyl 3-(hydroxymethyl)octahydro-1H-pyrrolo[2,3-c]pyridine-1-carboxylate, AcOH (contains some residual solvent, assume 100% yield for the purpose of calculating stoichiometry in next step). LCMS method A: retention time=1.74 min, M+H=257.25.

Step B3: 6-benzyl 1-tert-butyl 3-((tosyloxy)methyl)hexahydro-1H-pyrrolo[2,3-c]pyridine-1,6(2H)-dicarboxylate

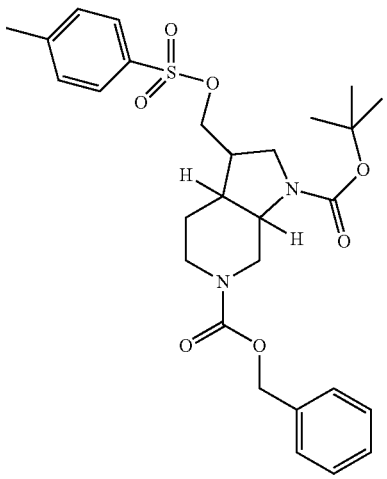 [SMILES: Cc1ccc(S(=O)(=O)OCC2CN(C(=O)OC(C)(C)C)C3CN(C(=O)OCc4ccccc4)CCC23)cc1]

THF (150 mL) and 10% aq. K2CO3 (150 mL, 109 mmol) were added to tert-butyl 3-(hydroxymethyl)octahydro-1H-pyrrolo[2,3-c]pyridine-1-carboxylate, AcOH (11.33 g, 35.8 mmol) with vigorous stirring. CBZ-Cl (5.37 mL, 37.6 mmol) was added and the mixture was stirred for 30 min. The mixture was poured into 200 mL chloroform, the layers separated, and the aqueous fraction extracted again with chloroform. The combined organics were washed with brine, dried over sodium sulfate, filtered and evaporated. The residue was redissolved in pyridine (75 mL), cooled on an ice bath and TsCl (6.34 g, 33.2 mmol) was added. The mixture was allowed to warm to ambient temperature and stirred overnight. The mixture was diluted with toluene and the bulk of the solvent was removed on the rotovap, then partitioned between ethyl acetate and 0.5M HCl (300 mL). The phases were separated and the organics were washed once more with brine, dried over sodium sulfate, filtered and evaporated to afford 6-benzyl 1-tert-butyl 3-((tosyloxy)methyl)hexahydro-1H-pyrrolo[2,3-c]pyridine-1,6(2H)-dicarboxylate (13.4 g, 81% yield) which was used without further purification. LCMS method A: retention time=4.11 min, M+H-Boc=445.25.

Step C: tert-butyl hexahydro-3,6-methanopyrrolo[2,3-c]pyridine-1(2H)-carboxylate

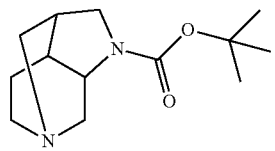 [SMILES: CC(C)(C)OC(=O)N1CC2CN3CCC2C1C3]

A solution of 6-benzyl 1-tert-butyl 3-((tosyloxy)methyl)hexahydro-1H-pyrrolo[2,3-c]pyridine-1,6(2H)-dicarboxylate (1.2 g, 2.2 mmol) in ethanol (50 mL) was added to a Parr bottle containing 10% palladium on carbon (200 mg) and the mixture was hydrogenated at 55 psi for 4 h, additional 10% palladium on carbon (100 mg) was added and the mixture was hydrogenated overnight.

A separate batch of 6-benzyl 1-tert-butyl 3-((tosyloxy)methyl)hexahydro-1H-pyrrolo[2,3-c]pyridine-1,6(2H)-dicarboxylate (2.5 g, 4.6 mmol) in ethanol (100 mL) was added to a separate Parr bottle containing 10% palladium on carbon (600 mg) and the mixture was hydrogenated at 55 psi overnight.

Both reactions were combined for purification: They were each filtered through celite, eluting with ethanol, and evaporated to dryness. The residue was purified by silica gel chromatography eluting with 5-10% (9:1 MeOH:NH4OH) in chloroform, affording some clean fractions along with some mixed fractions. The clean fractions were deemed to contain some residual tosic acid by HNMR and were therefore redissolved in chloroform and washed with saturated sodium carbonate, dried over sodium sulfate, filtered and evaporated to afford tert-butyl hexahydro-3,6-methanopyrrolo[2,3-c]pyridine-1(2H)-carboxylate (0.61 g, 36% yield). $^1$H NMR (500 MHz, CHLOROFORM-d) δ=3.94-3.64 (m, 1H), 3.37-2.67 (m, 6H), 2.60 (dd, J=2.1, 13.7 Hz, 1H), 2.20-2.08 (m, 1H), 2.08-1.96 (m, 1H), 1.80-1.61 (m, 2H), 1.54-1.41 (m, 9H).

Step D: (7-chlorobenzo[b]thiophen-2-yl)(hexahydro-3,6-methanopyrrolo[2,3-c]pyridin-1(2H)-yl)methanone

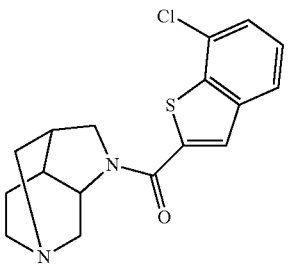 [SMILES: O=C(c1cc2cccc(Cl)c2s1)N1CC2CN3CCC2C1C3]

A solution of tert-butyl hexahydro-3,6-methanopyrrolo[2,3-c]pyridine-1(2H)-carboxylate (0.06 g, 0.25 mmol) in chloroform (1 mL) was treated with TFA (1 mL) and allowed to age for 15 min. and then evaporated. The residue was redissolved in DMF (1 mL), 7-chlorobenzo[b]thiophene-2-carboxylic acid (59 mg, 0.28 mmol), HATU (120 mg, 0.32 mmol) and DIPEA (0.2 mL, 1.15 mmol) were added. The mixture was allowed to stir at ambient temperature for 2 h and the residue was partitioned between chloroform and saturated aqueous sodium carbonate. The phases were separated and the aqueous fraction extracted twice more with chloroform. The combined organic phases were dried over sodium sulfate, filtered and the solvent was removed by evaporation on the rotovap. The resultant residue was purified by silica gel chromatography, eluting with a gradient from 5% to 40% (9:1 MeOH/NH4OH) in chloroform, affording (7-chlorobenzo[b]thiophen-2-yl)(hexahydro-3,6-methanopyrrolo[2,3-c]pyridin-1(2H)-yl)methanone (33 mg, 37% yield). LCMS method A: retention time: 3.12 min, M+H=333.1. $^1$H NMR (400 MHz, CHLOROFORM-d) δ=7.88-7.62 (m, 2H), 7.49-7.42 (m, 1H), 7.41-7.33 (m, 1H), 4.46-4.22 (m, 1H), 3.95-3.67 (m, 1H), 3.64-3.44 (m, 1H), 3.38-3.13 (m, 2H), 3.09-2.61 (m, 4H), 2.46-2.10 (m, 2H), 1.90-1.69 (m, 2H).

EXAMPLE 2

(hexahydro-3,6-methanopyrrolo[2,3-c]pyridin-1(2H)-yl)(1H-indazol-3-yl)methanone

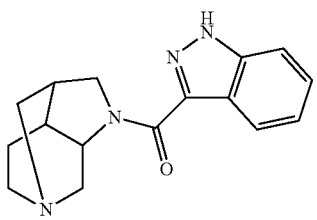 [SMILES: O=C(c1n[nH]c2ccccc12)N1CC2CN3CCC2C1C3]

Subjecting 1H-indazole-3-carboxylic acid (60 mg, 0.25 mmol) to the method of Example 1, step D, afforded (hexahydro-3,6-methanopyrrolo[2,3-c]pyridin-1(2H)-yl)(1H-indazol-3-yl)methanone (44 mg, 59% yield). LCMS method A: retention time=2.10 min, M+H=283.2. $^1$H NMR (400 MHz, CHLOROFORM-d) δ=13.92-11.11 (m, 1H), 8.92-8.10 (m, 1H), 7.61-7.33 (m, 2H), 7.32-7.18 (m, 1H), 4.75 (t, J=5.6 Hz, 1H), 4.10-3.49 (m, 3H), 3.43-3.15 (m, 2H), 3.11-2.65 (m, 3H), 2.47-1.99 (m, 2H), 1.97-1.66 (m, 2H).

EXAMPLE 3

(hexahydro-3,6-methanopyrrolo[2,3-c]pyridin-1(2H)-yl)(phenyl)methanone

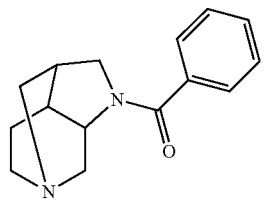 [SMILES: O=C(c1ccccc1)N1CC2CN3CCC2C1C3]

Step A: octahydro-3,6-methanopyrrolo[2,3-c]pyridine, 2 TFA

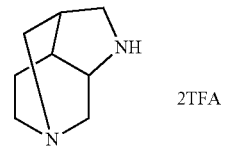

Tert-butyl hexahydro-3,6-methanopyrrolo[2,3-c]pyridine-1(2H)-carboxylate (830 mg, 3.48 mmol) was dissolved in chloroform (10 mL) and 2,2,2-trifluoroacetic acid (10 mL, 3.48 mmol) was added. The mixture was stirred 30 min and evaporated. The crude thick oil was placed under high vacuum for 4 h, at which point the mass appeared to be nearly constant, but the mass was greater than theoretical, which may have been due to excess TFA or water. The material was used as-is, assuming quantitative yield (3.49 mmol) for the purposes of calculating stoichiometry in the next steps. $^1$H NMR (400 MHz, DEUTERIUM OXIDE) δ=4.46-4.33 (m, 1H), 3.91-3.61 (m, 4H), 3.56 (d, J=15.1 Hz, 1H), 3.48-3.30 (m, 5H), 3.10-2.97 (m, 1H), 2.65 (t, J=4.4 Hz, 1H), 2.42-2.15 (m, 2H).

Step B: (hexahydro-3,6-methanopyrrolo[2,3-c]pyridin-1(2H)-yl)(phenyl)methanone

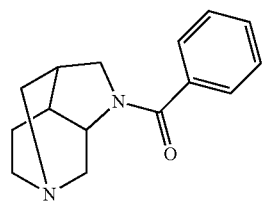 [SMILES: O=C(c1ccccc1)N1CC2CN3CCC2C1C3]

A stock solution was prepared by dissolving HATU (1.79 g, 4.7 mmol) and 23.5 mL of anhydrous DMF. It was sonicated until everything dissolved. In a separate vial containing benzoic acid (12 mg, 2.0 eq., 0.100 mmol) was added 0.5 mL of the HATU stock solution. The vials were shaken for 5 minutes. In another vial was added 1.25 g of octahydro-3,6-methanopyrrolo[2,3-c]pyridine, 2 TFA and 23.5 mL of anhydrous DMF. To this was added 2.05 mL of DIPEA. The vial was shaken for 5 minutes. Then to the vial containing the acid/HATU mixture was added 0.5 mL of the octahydro-3,6-methanopyrrolo[2,3-c]pyridine/DIPEA stock solution. The vials were shaken overnight at room temperature. The vials were transferred to a 96-well plate via the TECAN with two vessel rinses of 300 μL of DMF. Purification details are shown in Table 3.

EXAMPLES 4-86

The following examples were prepared according to the method described for the synthesis of example 3. Purification was performed by HPLC, using either a Sunfire C18 19×150 mm column (SF) or an X-bridge C18 19×150 mm column (XB), and eluting with a gradient of Methanol/Water containing 10 mM NH4OAc. The starting % MeOH is indicated in the table below, along with LCMS retention times and observed mass. For the indicated starting % methanol, the following gradients were employed:

| Time | B % | Flow |
|---|---|---|
| 5% Focused Gradient: | | |
| 0.00' | 5 | 10.0 |
| 3.50' | 5 | 20.0 |
| 11.80' | 30 | 20.0 |
| 12.80' | 40 | 20.0 |
| 12.90 | 99 | 20 |
| 16.40 | 99 | 20 |
| 16.60 | 5 | 20 |
| 10% Focused Gradient: | | |
| 0.00' | 10 | 10.0 |
| 3.50' | 10 | 20.0 |
| 11.80' | 35 | 20.0 |
| 12.80' | 45 | 20.0 |
| 12.90' | 99 | 20 |
| 16.40 | 99 | 20 |
| 16.60 | 10 | 20 |
| 20% Focused Gradient | | |
| 0.00' | 20 | 10.0 |
| 3.50' | 20 | 20.0 |
| 11.80' | 45 | 20.0 |
| 12.80' | 55 | 20.0 |
| 12.90' | 99 | 20 |
| 16.40 | 99 | 20 |
| 16.60 | 20 | 20 |
| 30% Focused Gradient | | |
| 0.00' | 30 | 10.0 |
| 3.50' | 30 | 20.0 |
| 11.80' | 55 | 20.0 |
| 12.80' | 65 | 20.0 |
| 12.90' | 99 | 20 |
| 16.40 | 99 | 20 |
| 16.60 | 30 | 20 |
| 40% Focused Gradient | | |
| 0.00' | 40 | 10.0 |
| 3.50' | 40 | 20.0 |
| 11.80' | 65 | 20.0 |
| 12.80' | 75 | 20.0 |
| 12.90' | 99 | 20 |
| 16.40 | 99 | 20 |
| 16.60 | 40 | 20 |
| 50% Focused Gradient | | |
| 0.00' | 50 | 10.0 |
| 3.50' | 50 | 20.0 |
| 11.80' | 75 | 20.0 |
| 12.80' | 85 | 20.0 |
| 12.90' | 99 | 20 |
| 16.40 | 99 | 20 |
| 16.60 | 40 | 20 |
| 60% Focused Gradient | | |
| 0.00' | 60 | 10.0 |
| 3.50' | 60 | 20.0 |
| 11.80' | 85 | 20.0 |
| 12.80' | 95 | 20.0 |
| 12.90' | 99 | 20 |
| 16.40 | 99 | 20 |
| 16.60 | 40 | 20 |

TABLE 1

Examples 3-86.

| Example number | R = | Column | MeOH Gradient start % | Observed MS | Retention time (min) | Mass (mg) |
|---|---|---|---|---|---|---|
| 3 | 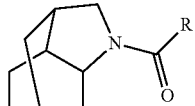 | SF | 10 | 242.32 | 1.44 | 3.62 |
| 4 | 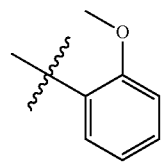 [SMILES: *c1ccccc1OC] | SF | 20 | 272.34 | 1.58 | 8.73 |
| 5 | 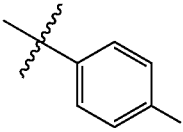 | SF | 30 | 276.76 | 1.98 | 6.75 |
| 6 | 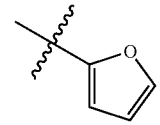 [SMILES: *c1ccco1] | SF | 10 | 232.28 | 1.15 | 4.52 |

TABLE 1-continued

Examples 3-86.

| Example number | R = | Column | MeOH Gradient start % | Observed MS | Retention time (min) | Mass (mg) |
|---|---|---|---|---|---|---|
| 7 | 2-bromofuran-5-yl | SF | 20 | 311.17 | 1.75 | 7.69 |
| 8 | naphthalen-1-yl | SF | 40 | 292.38 | 2.23 | 6.91 |
| 9 | naphthalen-2-yl | SF | 40 | 292.38 | 2.26 | 1.54 |
| 10 | furan-3-yl | SF | 5 | 232.28 | 1.1 | 7.18 |
| 11 | thiophen-2-yl | SF | 20 | 248.34 | 1.36 | 5.33 |
| 12 | 5-methylthiophen-2-yl | SF | 20 | 262.37 | 1.77 | 7.5 |
| 13 | thiophen-3-yl | SF | 20 | 248.34 | 1.3 | 6.8 |
| 14 | 1H-indol-2-yl | SF | 40 | 281.35 | 2.11 | 7.25 |
| 15 | benzo[d][1,3]dioxol-5-yl | SF | 20 | 286.33 | 1.49 | 7.62 |

TABLE 1-continued
Examples 3-86.
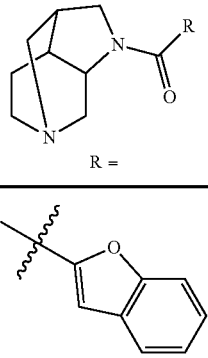
| Example number | R = | Column | MeOH Gradient start % | Observed MS | Retention time (min) | Mass (mg) |
|---|---|---|---|---|---|---|
| 16 | 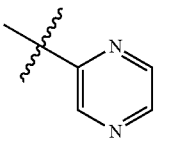 | SF | 30 | 282.34 | 2.14 | 6.52 |
| 17 | 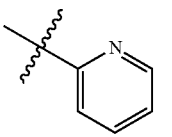 [SMILES: *c1ccccn1] | SF | 5 | 244.29 | 0.94 | 3.66 |
| 18 | 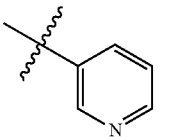 [SMILES: *c1cccnc1] | SF | 10 | 243.3 | 1.08 | 3.25 |
| 19 | 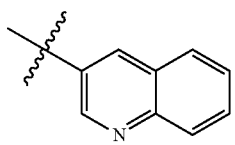 [SMILES: *c1cnc2ccccc2c1] | SF | 5 | 243.3 | 0.88 | 0.95 |
| 20 | 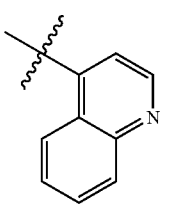 [SMILES: *c1ccnc2ccccc12] | SF | 20 | 293.36 | 1.67 | 3.96 |
| 21 | 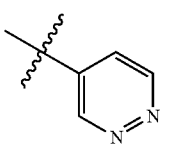 | SF | 20 | 293.36 | 1.6 | 8.43 |
| 22 | | SF | 5 | 244.29 | 1.38 | 2.15 |
| 23 | 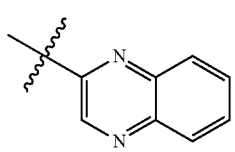 [SMILES: *c1cnc2ccccc2n1] | SF | 20 | 294.35 | 1.76 | 9.81 |

TABLE 1-continued

Examples 3-86.

| Example number | R = | Column | MeOH Gradient start % | Observed MS | Retention time (min) | Mass (mg) |
|---|---|---|---|---|---|---|
| 24 | 2,6-dimethylpyridinyl | SF | 10 | 257.33 | 1.38 | 6.95 |
| 25 | benzothiophen-2-yl | SF | 30 | 298.4 | 2.32 | 8.39 |
| 26 | 3-chlorothiophen-2-yl | SF | 20 | 282.79 | 1.69 | 6.58 |
| 27 | 5-methyl-2-phenyl-2H-1,2,3-triazol-4-yl | SF | 40 | 323.39 | 2.71 | 6.27 |
| 28 | 2-(pyridin-3-yl)thiazol-4-yl | SF | 20 | 326.42 | 1.7 | 6.65 |
| 29 | 1,2,3-thiadiazol-4-yl | SF | 5 | 250.32 | 0.99 | 5.64 |
| 30 | 5-methylpyrazin-2-yl | SF | 10 | 258.32 | 1.17 | 4.51 |
| 31 | 2-methoxypyridin-3-yl | SF | 10 | 273.33 | 1.28 | 8.1 |

TABLE 1-continued
Examples 3-86.
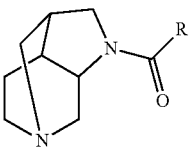
| Example number | R = | Column | MeOH Gradient start % | Observed MS | Retention time (min) | Mass (mg) |
|---|---|---|---|---|---|---|
| 32 | 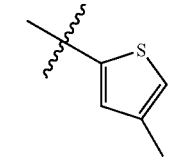 [SMILES: *c1cc(C)cs1] | SF | 20 | 262.37 | 1.75 | 7.48 |
| 33 | 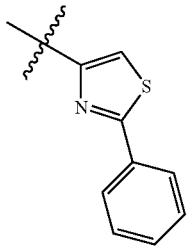 [SMILES: *c1csc(-c2ccccc2)n1] | SF | 10 | 299.39 | 1.4 | 8.16 |
| 34 | 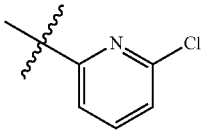 | SF | 40 | 325.43 | 2.55 | 11.02 |
| 35 | 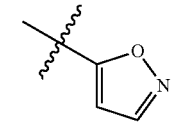 | SF | 20 | 277.75 | 1.55 | 7.41 |
| 36 | 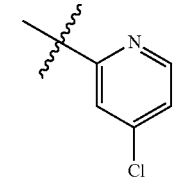 [SMILES: *c1cc(Cl)ccn1] | SF | 5 | 233.27 | 0.93 | 6.25 |
| 37 | 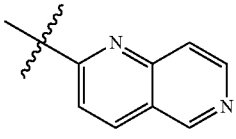 [SMILES: *c1ccc2cnccc2n1] | SF | 20 | 277.75 | 1.57 | 6.46 |
| 38 | 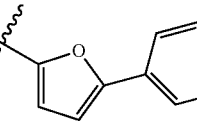 | SF | 10 | 294.35 | 1.36 | 4.69 |
| 39 |  | SF | 40 | 308.37 | 2.52 | 10.34 |

TABLE 1-continued
Examples 3-86.
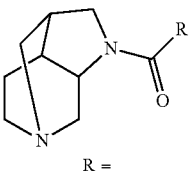
| Example number | R = | Column | MeOH Gradient start % | Observed MS | Retention time (min) | Mass (mg) |
| --- | --- | --- | --- | --- | --- | --- |
| 40 | 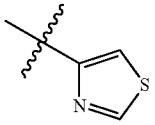 [SMILES: *c1cscn1] | SF | 5 | 249.33 | 1.05 | 7.19 |
| 41 | 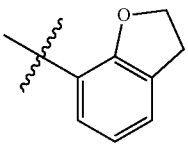 [SMILES: *c1cccc2c1OCC2] | SF | 20 | 284.35 | 1.63 | 10.7 |
| 42 | 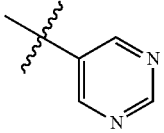 [SMILES: *c1cncnc1] | SF | 5 | 244.29 | 0.8 | 5.95 |
| 43 | 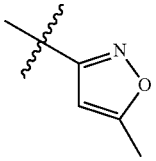 [SMILES: *c1cc(C)on1] | SF | 10 | 247.29 | 1.34 | 5.19 |
| 44 | 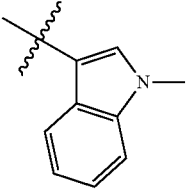 [SMILES: *c1cn(C)c2ccccc12] | SF | 20 | 295.38 | 1.87 | 9.25 |
| 45 | 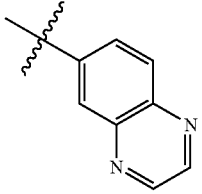 [SMILES: *c1ccc2nccnc2c1] | SF | 10 | 294.35 | 1.31 | 7.3 |
| 46 | 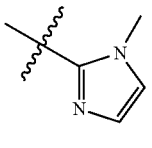 [SMILES: *c1nccn1C] | SF | 5 | 246.31 | 1.05 | 7.96 |
| 47 | 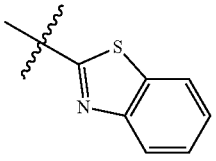 [SMILES: *c1nc2ccccc2s1] | SF | 30 | 299.39 | 2.37 | 9.68 |

TABLE 1-continued
Examples 3-86.
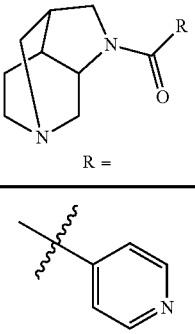
| Example number | R = | Column | MeOH Gradient start % | Observed MS | Retention time (min) | Mass (mg) |
|---|---|---|---|---|---|---|
| 48 | 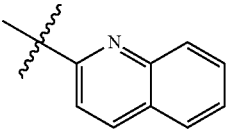 [SMILES: *c1ccc2ccccc2n1] | SF | 5 | 243.3 | 1.25 | 4.84 |
| 49 | 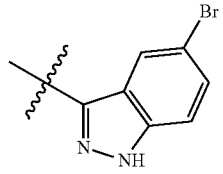 [SMILES: *c1n[nH]c2ccc(Br)cc12] | SF | 20 | 293.36 | 2.02 | 9.42 |
| 50 | 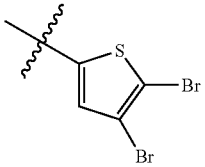 [SMILES: *c1cc(Br)c(Br)s1] | XB | 40 | 361.01 | 2.34 | 6.71 |
| 51 | 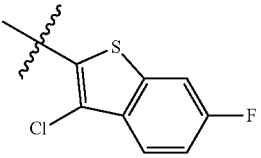 [SMILES: *c1sc2cc(F)ccc2c1Cl] | XB | 50 | 406.86 | 2.68 | 6.95 |
| 52 | 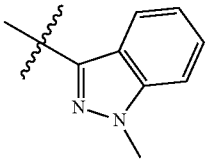 [SMILES: *c1nn(C)c2ccccc12] | XB | 50 | 351.03 | 2.73 | 3.52 |
| 53 | 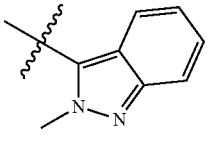 [SMILES: *c1c2ccccc2nn1C] | XB | 40 | 297.13 | 1.95 | 2.94 |
| 54 | 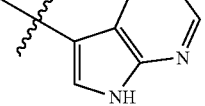 | XB | 30 | 297.13 | 1.8 | 5.68 |
| 55 | | SF | 10 | 283.12 | 1.29 | 11.63 |

TABLE 1-continued
Examples 3-86.
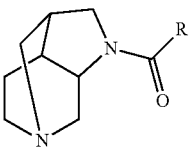
| Example number | R = | Column | MeOH Gradient start % | Observed MS | Retention time (min) | Mass (mg) |
| --- | --- | --- | --- | --- | --- | --- |
| 56 | 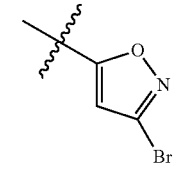 [SMILES: *c1cc(Br)no1] | SF | 20 | 311.99 | 1.49 | 9.62 |
| 57 | 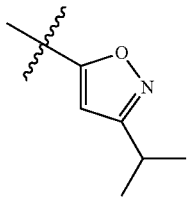 [SMILES: *c1cc(C(C)C)no1] | SF | 30 | 390.89 | 1.14 | 9.61 |
| 58 | 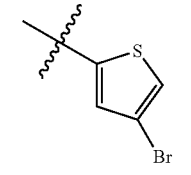 [SMILES: *c1cc(Br)cs1] | SF | 20 | 276.44 | 0.92 | 10.33 |
| 59 | 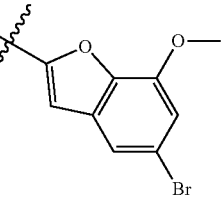 | SF | 30 | 328.96 | 0.69 | 11.06 |
| 60 | 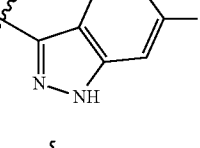 | SF | 50 | 391.01 | 2.8 | 5.77 |
| 61 | 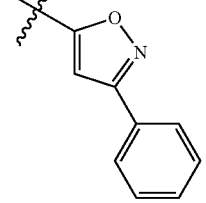 | SF | 30 | 313.11 | 1.83 | 3.03 |
| 62 |  | SF | 50 | 310.11 | 2.57 | 4.84 |

TABLE 1-continued
Examples 3-86.
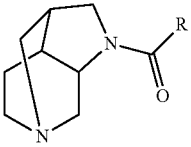
| Example number | R = | Column | MeOH Gradient start % | Observed MS | Retention time (min) | Mass (mg) |
|---|---|---|---|---|---|---|
| 63 | 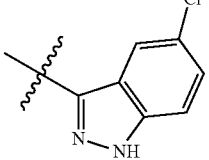 | SF | 40 | 317.07 | 2.23 | 5.81 |
| 64 | 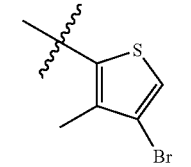 [SMILES: *c1scc(Br)c1C] | SF | 20 | 248.1 | 1.18 | 5.28 |
| 65 | 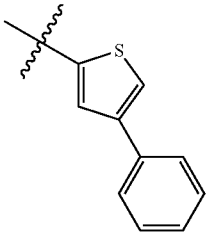 [SMILES: *c1cc(-c2ccccc2)cs1] | SF | 40 | 342.97 | 2.21 | 1.38 |
| 66 | 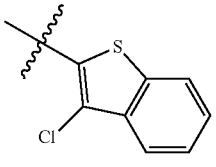 [SMILES: *c1sc2ccccc2c1Cl] | SF | 50 | 325.09 | 2.63 | 5.07 |
| 67 | 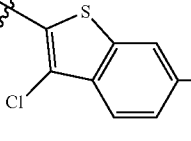 | SF | 50 | 333.03 | 2.65 | 5.75 |
| 68 | 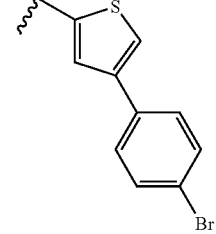 | SF | 60 | 347.05 | 3 | 3.64 |
| 69 |  | SF | 60 | 404.99 | 3.11 | 7.25 |

TABLE 1-continued
Examples 3-86.
| Example number | R = | Column | MeOH Gradient start % | Observed MS | Retention time (min) | Mass (mg) |
|---|---|---|---|---|---|---|
| 70 | 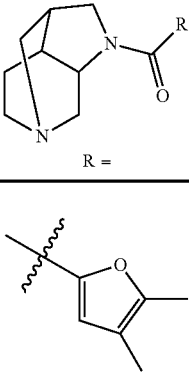 | SF | 30 | 260.82 | 1.8 | 9.06 |
| 71 | 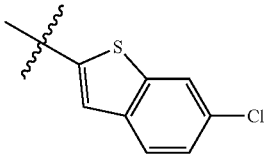 [SMILES: *c1cc2ccc(Cl)cc2s1] | SF | 50 | 333.03 | 2.8 | 13.65 |
| 72 | 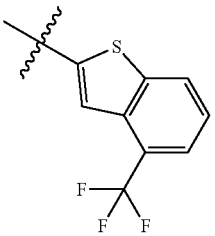 [SMILES: *c1cc2c(C(F)(F)F)cccc2s1] | SF | 50 | 366.86 | 2.93 | 13.29 |
| 73 | 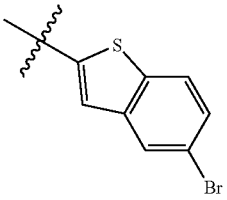 [SMILES: *c1cc2cc(Br)ccc2s1] | SF | 50 | 378.97 | 2.85 | 7.11 |
| 74 | 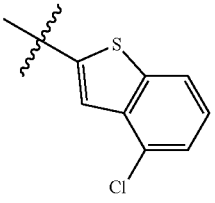 [SMILES: *c1cc2c(Cl)cccc2s1] | SF | 50 | 333.03 | 2.78 | 6.75 |
| 75 | 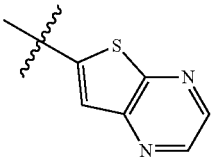 [SMILES: *c1cc2nccnc2s1] | SF | 20 | 301.05 | 1.42 | 1.33 |
| 76 | 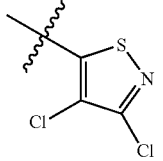 [SMILES: *c1snc(Cl)c1Cl] | SF | 40 | 317.98 | 3.61 | 3.37 |

TABLE 1-continued
Examples 3-86.
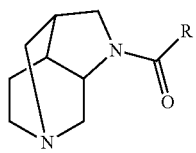
| Example number | R = | Column | MeOH Gradient start % | Observed MS | Retention time (min) | Mass (mg) |
|---|---|---|---|---|---|---|
| 77 | 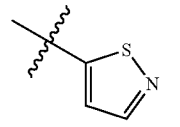 [SMILES: *c1ccns1] | SF | 20 | 313.12 | 1.59 | 8.22 |
| 78 | 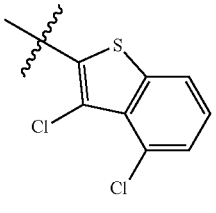 [SMILES: *c1sc2cccc(Cl)c2c1Cl] | SF | 10 | 250.05 | 1.07 | 7.11 |
| 79 | 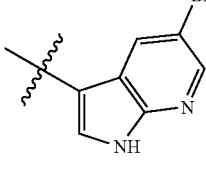 | SF | 60 | 366.99 | 2.95 | 4.67 |
| 80 | 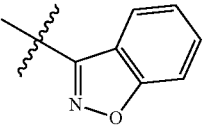 [SMILES: *c1noc2ccccc12] | SF | 30 | 361.01 | 1.95 | 1.01 |
| 81 | 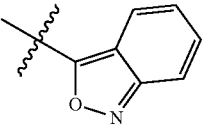 [SMILES: *c1onc2ccccc12] | SF | 40 | 284.12 | 2.07 | 10.19 |
| 82 | 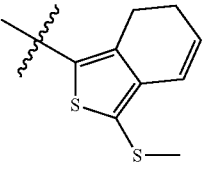 [SMILES: *c1sc(SC)c2c1CCC=C2] | SF | 30 | 284.11 | 1.89 | 1.49 |
| 83 | | SF | 60 | 347.08 | 2.96 | 7.57 |

TABLE 1-continued

Examples 3-86.

| Example number | R = | Column | MeOH Gradient start % | Observed MS | Retention time (min) | Mass (mg) |
|---|---|---|---|---|---|---|
| 84 | | SF | 60 | 359.04 | 3.03 | 4.84 |
| 85 | | SF | 50 | 351.03 | 2.68 | 2.00 |
| 86 | | SF | 60 | 347.04 | 2.94 | 9.05 |

EXAMPLE 87

((3S,3aS,6R,7aR)-hexahydro-3,6-methanopyrrolo[2,3-c]pyridin-1(2H)-yl)(1H-indazol-3-yl)methanone

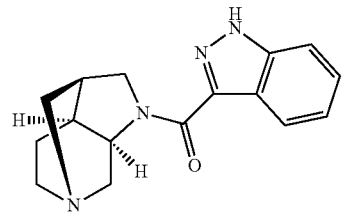 [SMILES: O=C(c1n[nH]c2ccccc12)N1C[C@@H]2C[N@@]3CC[C@@H]2[C@@H]1C3]

Step A: (S)-tert-butyl 3-(hydroxymethyl)-2,3-dihydro-1H-pyrrolo[2,3-c]pyridine-1-carboxylate and (R)-tert-butyl 3-(hydroxymethyl)-2,3-dihydro-1H-pyrrolo[2,3-c]pyridine-1-carboxylate

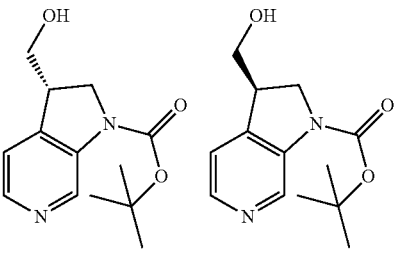

Chiral SFC separation was performed on tert-butyl 3-(hydroxymethyl)-2,3-dihydro-1H-pyrrolo[2,3-c]pyridine-1-carboxylate (~6.5 g). Conditions: Column=Chiralpak AD-H 30×250 mm, Sum; Mobile phase=15% Methanol with 0.1%

DEA in CO2; Temp=35° C.; Pressure=150 bar; flow rate=70 mL/min; UV monitored at 215 nm; injection: ~1 mL of a ~30 mg/mL solution in MeOH. Peak 1 was believed to be (S)-tert-butyl 3-(hydroxymethyl)-2,3-dihydro-1H-pyrrolo[2,3-c]pyridine-1-carboxylate (2.70 g). $^1$H NMR (400 MHz, CHLOROFORM-d) δ=9.31-8.56 (m, 1H), 8.26 (d, J=4.8 Hz, 1H), 7.25-7.16 (m, 1H), 4.17-4.05 (m, 1H), 3.85 (t, J=5.5 Hz, 3H), 3.63-3.54 (m, 1H), 1.76-1.69 (m, 1H), 1.60 (d, J=9.5 Hz, 9H). Peak 2 was believed to be (R)-tert-butyl 3-(hydroxymethyl)-2,3-dihydro-1H-pyrrolo[2,3-c]pyridine-1-carboxylate (2.69 g). $^1$H NMR (400 MHz, CHLOROFORM-d) δ=9.25-8.52 (m, 1H), 8.23 (d, J=4.8 Hz, 1H), 7.21 (d, J=4.3 Hz, 1H), 4.21-4.03 (m, 1H), 3.97-3.78 (m, 3H), 3.56 (dd, J=5.8, 10.0 Hz, 1H), 2.26-2.05 (m, 1H), 1.60 (br. s., 9H).

Step B: (R)-tert-butyl 3-(((triisopropylsilyl)oxy)methyl)-2,3-dihydro-1H-pyrrolo[2,3-c]pyridine-1-carboxylate

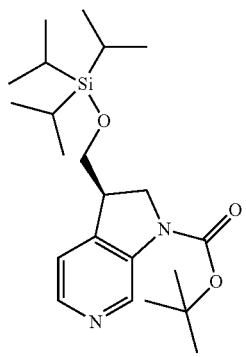 [SMILES: CC(C)[Si](OC[C@H]1CN(C(=O)OC(C)(C)C)c2cnccc21)(C(C)C)C(C)C]

A solution of (R)-tert-butyl 3-(hydroxymethyl)-2,3-dihydro-1H-pyrrolo[2,3-c]pyridine-1-carboxylate (2.69 g, 10.8 mmol) in DMF (10 mL) was reacted with TIPS-Cl (2.5 g, 12.9 mmol) and imidazole (0.88 g, 12.9 mmol). The mixture was stirred for 3 h, evaporated and then purified by silica gel chromatography, eluting with a gradient from 12-100% EtOAc in hexanes, affording (R)-tert-butyl 3-(((triisopropylsilyl)oxy)methyl)-2,3-dihydro-1H-pyrrolo[2,3-c]pyridine-1-carboxylate (3.9 g, 88% yield). LCMS Method A, Retention time=4.69 min, M+H=407.3.

Step C: (3R,3aS,7aR)-tert-butyl 3-(((triisopropylsilyl)oxy)methyl)octahydro-1H-pyrrolo[2,3-c]pyridine-1-carboxylate

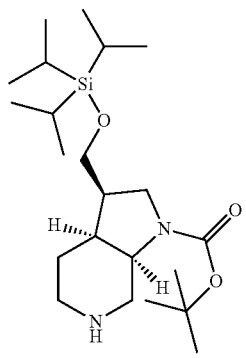 [SMILES: CC(C)[Si](OC[C@H]1CN(C(=O)OC(C)(C)C)[C@H]2CNCC[C@@H]12)(C(C)C)C(C)C]

In a parr flask was added tert-butyl 3-(((triisopropylsilyl)oxy)methyl)-2,3-dihydro-1H-pyrrolo[2,3-c]pyridine-1-carboxylate (3.9 g, 9.59 mmol) and platinum(IV) oxide (0.5 g, 2.202 mmol) in Ethanol (40 mL) and Acetic Acid (10 mL). The flask was charged to 55 PSI of Hydrogen on the Parr and allowed to shake overnight. The reaction was filtered through celite and concentrated to remove all the ethanol and still had residual acetic acid this was used as-is in the next reaction. LCMS Method A, Retention time=4.36 min, M+H=413.4. Yield of (3R,3aS,7aR)-tert-butyl 3-(((triisopropylsilyl)oxy)methyl)octahydro-1H-pyrrolo[2,3-c]pyridine-1-carboxylate was assumed to be quantitative for the purposes of calculating stoichiometry in next step.

Step D: (3R,3aS,7aR)-6-benzyl 1-tert-butyl 3-(((triisopropylsilyl)oxy)methyl) hexahydro-1H-pyrrolo[2,3-c]pyridine-1,6(2H)-dicarboxylate

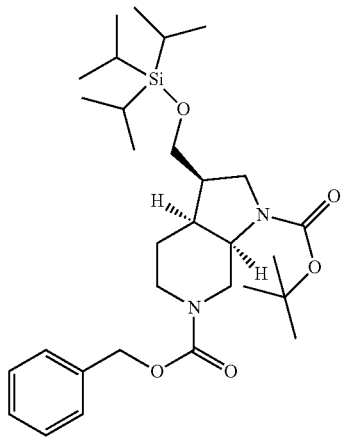 [SMILES: CC(C)[Si](OC[C@H]1CN(C(=O)OC(C)(C)C)[C@H]2CN(C(=O)OCc3ccccc3)CC[C@@H]12)(C(C)C)C(C)C]

A flask was charged with a solution of (3R,3aS,7aR)-tert-butyl 3-(((triisopropylsilyl)oxy)methyl)octahydro-1H-pyrrolo[2,3-c]pyridine-1-carboxylate (assume 3.96 g, 9.59 mmol; containing some AcOH, yield assumed to be quantitative from previous step) in THF (60 mL). To this was added 10% aq. K2CO3 (60 mL, 43.4 mmol) and CBZ-Cl (1.437 mL, 10.07 mmol). The reaction was allowed to stir at room temperature. After 1 hour the reaction was diluted with chloroform and saturated sodium bicarbonate. The organic was collected and purified by silica gel chromatography eluting in 10%-100% Ethyl acetate in hexanes. (3R,3aS,7aR)-6-benzyl 1-tert-butyl 3-(((triisopropylsilyl)oxy)methyl) hexahydro-1H-pyrrolo[2,3-c]pyridine-1,6(2H)-dicarboxylate (4.2 g, 80% yield). LCMS Method A: retention time=4.09 min, M+H-Boc=445.25.

Step E: (3R,3aS,7aR)-6-benzyl 1-tert-butyl 3-(hydroxymethyl)hexahydro-1H-pyrrolo[2,3-c]pyridine-1,6(2H)-dicarboxylate

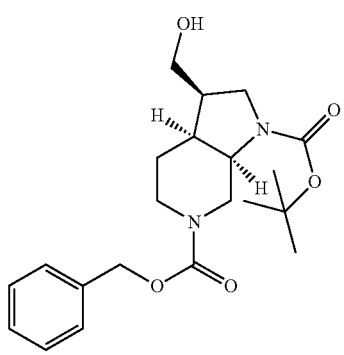 [SMILES: CC(C)(C)OC(=O)N1C[C@H](CO)[C@@H]2CCN(C(=O)OCc3ccccc3)C[C@@H]21]

A flask was charged with (3R,3aS,7aR)-6-benzyl 1-tert-butyl 3-(((triisopropylsilyl)oxy)methyl)hexahydro-1H-pyrrolo[2,3-c]pyridine-1,6(2H)-dicarboxylate (4.2 g, 7.68 mmol) in tetrahydrofuran (15 mL). To this was added TBAF (7.68 mL, 7.68 mmol). The reaction was then allowed to stir at room temperature for 3 hours and then poured into chloroform and water. The organic was collected and concentrated to residue. This was used as is for next reaction. LCMS Method A: retention time=3.59 min, M+H-Boc=391.3.

Step F: (3R,3aS,7aR)-6-benzyl 1-tert-butyl 3-((tosyloxy)methyl)hexahydro-1H-pyrrolo[2,3-c]pyridine-1,6(2H)-dicarboxylate

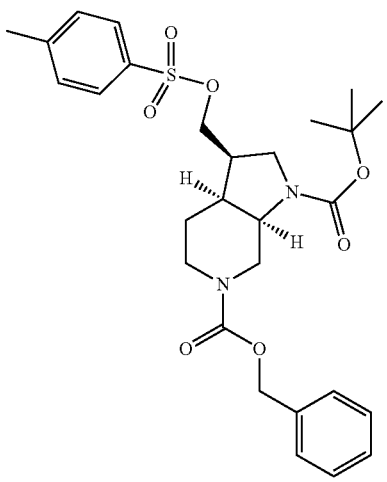 [SMILES: Cc1ccc(S(=O)(=O)OC[C@H]2CN(C(=O)OC(C)(C)C)[C@H]3CN(C(=O)OCc4ccccc4)CC[C@@H]23)cc1]

A flask was charged with (3R,3aS,7aR)-6-benzyl 1-tert-butyl 3-(hydroxymethyl)hexahydro-1H-pyrrolo[2,3-c]pyridine-1,6(2H)-dicarboxylate (3.0 g, 7.68 mmol) and 4-methylbenzene-1-sulfonyl chloride (1.758 g, 9.22 mmol) in Pyridine (20 mL). The reaction was allowed to stir overnight and then concentrated to residue. Taken up in toluene and concentrated again. This was flashed in the Biotage to give (3R,3aS,7aR)-6-benzyl 1-tert-butyl 3-((tosyloxy)methyl)hexahydro-1H-pyrrolo[2,3-c]pyridine-1,6(2H)-dicarboxylate (3.41 g, 81% yield). LCMS Method A: retention time=4.14 min, M+H-Boc=445.25.

The following alternate method was also employed for the synthesis of (3R,3aS,7aR)-6-benzyl 1-tert-butyl 3-((tosyloxy)methyl)hexahydro-1H-pyrrolo[2,3-c]pyridine-1,6(2H)-dicarboxylate:

Step G: (3S,3aR,7aS)-6-benzyl 1-tert-butyl 3-((tosyloxy)methyl)hexahydro-1H-pyrrolo[2,3-c]pyridine-1,6(2H)-dicarboxylate and (3R,3aS,7aR)-6-benzyl 1-tert-butyl 3-((tosyloxy)methyl)hexahydro-1H-pyrrolo[2,3-c]pyridine-1,6(2H)-dicarboxylate

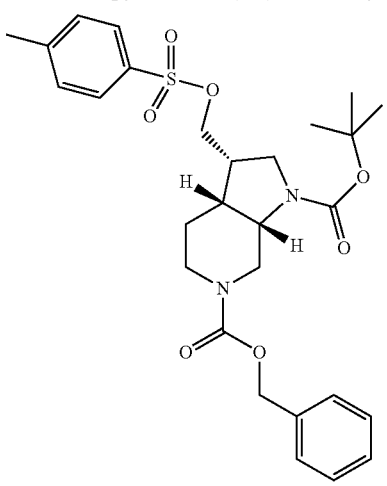

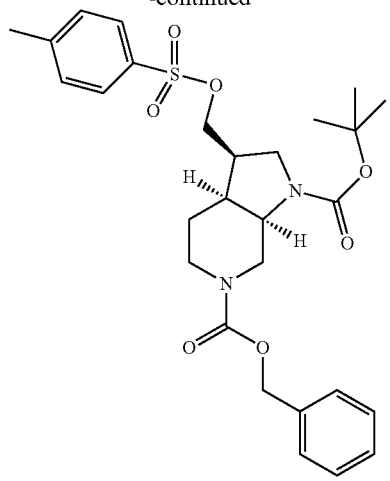

Chiral SFC separation was performed on 6-benzyl 1-tert-butyl 3-((tosyloxy)methyl)hexahydro-1H-pyrrolo[2,3-c]pyridine-1,6(2H)-dicarboxylate (racemic mixture of diastereomers) (~10 g). Conditions: Column=Chiralpak AD-H 30×250 mm, 5um; Mobile phase=20% Methanol in CO2; Temp=35° C.; Pressure=150 bar; flow rate=70 mL/min; UV monitored at 220 nm; injection: ~1 mL of a ~20 mg/mL solution in MeOH. (3S,3aR,7aS)-6-benzyl 1-tert-butyl 3-((tosyloxy)methyl)hexahydro-1H-pyrrolo[2,3-c]pyridine-1,6(2H)-dicarboxylate (4.6 g,) and the second peak was believed to be (3R,3aS,7aR)-6-benzyl 1-tert-butyl 3-((tosyloxy)methyl)hexahydro-1H-pyrrolo[2,3-c]pyridine-1,6 (2H)-dicarboxylate (4.7 g). Both enantiomers contained small amounts of minor diastereomers, but were taken on as-is.

Step H: (3S,3aS,6R,7aR)-tert-butyl hexahydro-3,6-methanopyrrolo[2,3-c]pyridine-1(2H)-carboxylate

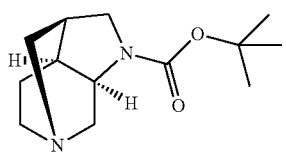 [SMILES: CC(C)(C)OC(=O)N1C[C@@H]2C[N@@]3CC[C@@H]2[C@@H]1C3]

In a Parr flask was added (3R,3aS,7aR)-6-benzyl 1-tert-butyl 3-((tosyloxy)methyl)hexahydro-1H-pyrrolo[2,3-c]pyridine-1,6(2H)-dicarboxylate (3.4 g, 6.24 mmol) in ethanol (50 mL) and ethyl acetate (5 mL). The solution was then treated with 10% palladium on carbon (0.664 g, 6.24 mmol) and the reaction was placed on the Parr shaker. The Parr was charged to 50 PSI of Hydrogen and then the reaction mixture was shaken overnight. The reaction vessel was then purged with nitrogen and the reaction was filtered thru a pad of celite. The resulting filtrate was concentrated to a residue and then take up in chloroform. The organic was washed with saturated $Na_2CO_3$ and the organic was collected. The organic was concentrated to afford (3S,3aS,6R,7aR)-tert-butyl hexahydro-3,6-methanopyrrolo[2,3-c]pyridine-1(2H)-carboxylate (1.2 g, 81% yield). $^1$H NMR (400 MHz, DMSO-$d_6$) δ=3.64 (s, 1H), 2.98 (s, 4H), 2.75-2.56 (m, 2H), 2.43 (d, J=14.6 Hz, 2H), 2.08 (br. s., 1H), 2.02-1.90 (m, 1H), 1.59 (d, J=3.3 Hz, 2H), 1.48-1.37 (m, 9H).

Step I: ((3S,3aS,6R,7aR)-hexahydro-3, 6-methano-pyrrolo[2,3-c]pyridin-1(2H)-yl) (1H-indazol-3-yl)methanone

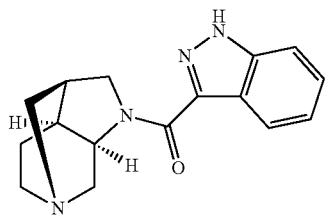 [SMILES: O=C(c1n[nH]c2ccccc12)N1C[C@@H]2C[N@@]3CC[C@@H]2[C@@H]1C3]

In a vial was added (3S,3aS,6R,7aR)-tert-butyl hexahydro-3,6-methanopyrrolo[2,3-c]pyridine-1(2H)-carboxylate (95 mg, 0.399 mmol) and dichloromethane (1 mL) and TFA (1 ml, 12.98 mmol). This was stirred at room temperature for 2 hours and then concentrated to residue. The residue was then taken up in DMF (1 ml) and treated with 1H-indazole-3-carboxylic acid (64.6 mg, 0.399 mmol), N-ethyl-N-isopropylpropan-2-amine (0.208 ml, 1.196 mmol) and 2-(3H-[1,2,3]triazolo[4,5-b]pyridin-3-yl)-1,1,3,3-tetramethylisouronium hexafluorophosphate(V) (152 mg, 0.399 mmol). The mixture was stirred at room temperature overnight and then poured into water and chloroform. The organic was collected and purified on the biotage eluting in 10%-30%(10% NH$_4$OH/Methanol) in chloroform. The product was collected and concentrated to a white solid. LCMS Method A: retention time=2.02 min, M+H=283.2. $^1$H NMR (400 MHz, CHLOROFORM-d) δ=8.36 (d, J=8.3 Hz, 1H), 7.60-7.51 (m, 1H), 7.47-7.36 (m, 1H), 4.99-4.45 (m, 1H), 3.90 (s, 1H), 3.74 (dd, J=4.0, 11.8 Hz, 1H), 3.59 (d, J=11.8 Hz, 1H), 3.53-2.86 (m, 6H), 2.04 (s, 11H).

EXAMPLE 88

((3R,3aR,6S,7aS)-hexahydro-3,6-methanopyrrolo[2,3-c]pyridin-1(2H)-yl)(1H-indazol-3-yl)methanone

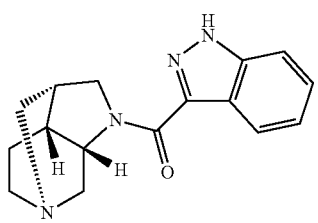 [SMILES: O=C(c1n[nH]c2ccccc12)N1C[C@H]2C[N@]3CC[C@H]2[C@H]1C3]

Step A: (3R,3aR,6S,7aS)-tert-butyl hexahydro-3,6-methanopyrrolo[2,3-c]pyridine-1(2H)-carboxylate

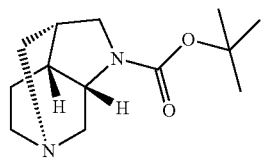 [SMILES: CC(C)(C)OC(=O)N1C[C@H]2C[N@]3CC[C@H]2[C@H]1C3]

Using the opposite enantiomer from the chiral separation, (3R,3aR,6S,7aS)-tert-butyl hexahydro-3,6-methanopyrrolo[2,3-c]pyridine-1(2H)-carboxylate was prepared according to the methods of example 87. $^1$H NMR (400 MHz, CHLOROFORM-d) δ=4.00-3.61 (m, 1H), 3.47-2.50 (m, 7H), 2.25-2.08 (m, 1H), 2.08-1.90 (m, 2H), 1.81-1.59 (m, 2H), 1.57-1.29 (m, 9H).

Step B: ((3R,3aR,6S,7aS)-hexahydro-3,6-methanopyrrolo[2,3-c]pyridin-1(2H)-yl) (1H-indazol-3-yl)methanone

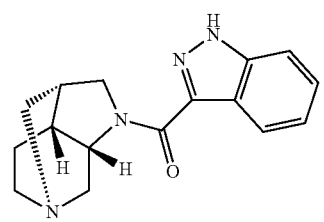 [SMILES: O=C(c1n[nH]c2ccccc12)N1C[C@H]2C[N@]3CC[C@H]2[C@H]1C3]

Following the method of example 87, step I, (3R,3aR,6S,7aS)-tert-butyl hexahydro-3,6-methanopyrrolo[2,3-c]pyridine-1(2H)-carboxylate was converted to ((3R,3aR,6S,7aS)-hexahydro-3,6-methanopyrrolo[2,3-c]pyridin-1(2H)-yl)(1H-indazol-3-yl)methanone. LCMS Method A: retention time=2.04 min, M+H=283.2. $^1$H NMR (400 MHz, CHLOROFORM-d) δ=11.75-10.05 (m, 1H), 8.37 (d, J=8.3 Hz, 1H), 7.62-7.52 (m, 1H), 7.47-7.38 (m, 1H), 4.92-4.47 (m, 1H), 4.03-3.88 (m, 1H), 3.83-3.57 (m, 2H), 3.47-2.73 (m, 7H), 2.03 (s, 7H) (some signals obscured by solvent/water peaks).

The following examples (89-99) were prepared from (3R,3aR,6S,7aS)-tert-butyl hexahydro-3,6-methanopyrrolo[2,3-c]pyridine-1(2H)-carboxylate according to the method of example 3:

EXAMPLE 89: benzo[b]thiophen-2-yl((3R,3aR,6S,7aS)-hexahydro-3,6-methanopyrrolo[2,3-c]pyridin-1(2H)-yl)methanone

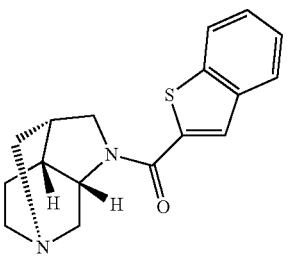 [SMILES: O=C(c1cc2ccccc2s1)N1C[C@H]2C[N@]3CC[C@H]2[C@H]1C3]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 60-90% B over 30 minutes, then a 5-minute hold at 100% B; Flow: 20 mL/min. Fractions containing the desired product were combined and dried via centrifugal evaporation. The yield of the product was 6.9 mg, and its estimated purity by LCMS analysis was 92%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.78 min, M+H=299.11. Proton NMR was acquired in deuterated DMSO. $^1$H NMR (400 MHz, DMSO-$d_6$) δ=8.07-7.91 (m, 3H), 7.54-7.38 (m, 2H), 4.41-4.15 (m, 1H), 3.98-3.52 (m, 2H), 2.86-2.62 (m, 5H), 2.46-2.13 (m, 2H), 1.85-1.63 (m, 2H) (some signals obscured by water peak).

EXAMPLE 90: ((3R,3aR,6S,7aS)-hexahydro-3,6-methanopyrrolo[2,3-c]pyridin-1(2H)-yl)(1-methyl-1H-indazol-3-yl)methanone

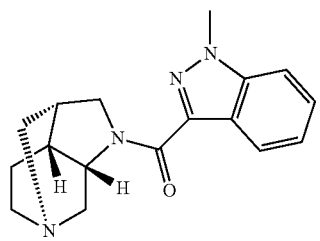 [SMILES: Cn1nc(C(=O)N2C[C@H]3C[N@]4CC[C@H]3[C@H]2C4)c2ccccc21]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 15-45% B over 30 minutes, then a 5-minute hold at 100% B; Flow: 20 mL/min. Fractions containing the desired product were combined and dried via centrifugal evaporation. The yield of the product was 8.7 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.41 min, M+H=297.16. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-$d_6$) δ=8.26-8.17 (m, 1H), 7.73 (td, J=0.8, 8.5 Hz, 1H), 7.48 (s, 1H), 7.27 (d, J=0.9 Hz, 1H), 4.71 (s, 1H), 4.17-4.12 (m, 3H), 3.96-3.77 (m, 1H), 2.87-2.68 (m, 3H), 2.40-2.24 (m, 1H), 2.19-2.06 (m, 1H), 1.73 (dd, J=2.6, 8.4 Hz, 1H) (some signals obscured by solvent/water peaks).

EXAMPLE 91: ((3R,3aR,6S,7aS)-hexahydro-3,6-methanopyrrolo[2,3-c]pyridin-1(2H)-yl)(1-methyl-1H-indol-3-yl)methanone

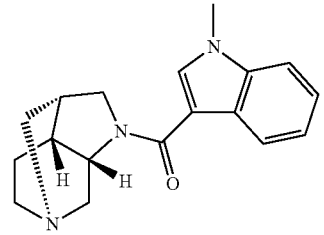 [SMILES: Cn1cc(C(=O)N2C[C@H]3C[N@]4CC[C@H]3[C@H]2C4)c2ccccc21]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 60-90% B over 30 minutes, then a 5-minute hold at 100% B; Flow: 20 mL/min. Fractions containing the desired product were combined and dried via centrifugal evaporation. The yield of the product was 6.9 mg, and its estimated purity by LCMS analysis was 92%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.39 min, M+H=296.17. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (400 MHz, DMSO-$d_6$) δ=8.25-8.09 (m, 1H), 7.49 (d, J=8.0 Hz, 1H), 7.24 (ddd, J=1.3, 7.1, 8.2 Hz, 1H), 7.14 (ddd, J=1.0, 7.0, 8.0 Hz, 1H), 4.17 (t, J=5.9 Hz, 1H), 3.86 (s, 3H), 3.20-3.09 (m, 2H), 2.77-2.62 (m, 4H), 2.08 (br. s., 2H), 1.69 (br. s., 2H) (some signals obscured by solvent/water peaks).

EXAMPLE 92: ((3R,3aR,6S,7aS)-hexahydro-3,6-methanopyrrolo[2,3-c]pyridin-1(2H)-yl)(5-chloro-1H-indazol-3-yl)methanone

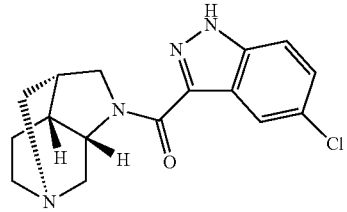 [SMILES: O=C(c1n[nH]c2ccc(Cl)cc12)N1C[C@H]2C[N@]3CC[C@H]2[C@H]1C3]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 15-45% B over 30 minutes, then a 5-minute hold at 100% B; Flow: 20 mL/min. Fractions containing the desired product were combined and dried via centrifugal evaporation. The yield of the product was 5.7 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.56 min, M+H=317.11. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (400 MHz, DMSO-$d_6$) δ=8.25-8.17 (m, 1H), 7.71-7.64 (m, 1H), 7.45 (d, J=2.3 Hz, 1H), 4.76-4.20 (m, 1H), 3.93-3.73 (m, 1H), 3.55-3.48 (m, 1H), 3.17-2.98 (m, 3H), 2.74-2.61 (m, 3H), 2.37-2.04 (m, 3H), 1.75-1.63 (m, 2H).

EXAMPLE 93: ((3R,3aR,6S,7aS)-hexahydro-3,6-methanopyrrolo[2,3-c]pyridin-1(2H)-yl)(6-methoxy-1H-indazol-3-yl)methanone

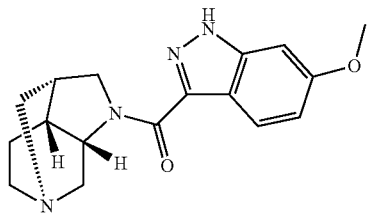 [SMILES: COc1ccc2c(C(=O)N3C[C@H]4C[N@]5CC[C@H]4[C@H]3C5)n[nH]c2c1]

The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 30-100% B over 13 minutes, then a 3-minute hold at 100% B; Flow: 20 mL/min. Fractions containing the desired product were combined and dried via centrifugal evaporation. The yield of the product was 6.9 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=2.36 min, M+H=313.16. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-$d_6$) δ=13.36-13.27 (m, 1H), 8.03 (dd, J=4.9, 8.9 Hz, 1H), 6.97 (dd, J=2.1, 3.7 Hz, 1H), 6.90-6.80 (m, 1H), 4.83-4.22 (m, 1H), 3.85 (s, 4H), 3.59-3.47 (m, 1H), 3.25-3.10 (m, 2H), 2.74 (s, 3H), 2.44-2.08 (m, 2H), 1.81-1.65 (m, 2H).

EXAMPLE 94: 4-chlorobenzo[b]thiophen-2-yl((3R,3aR,6S,7aS)-hexahydro-3,6-methanopyrrolo[2,3-c]pyridin-1(2H)-yl)methanone

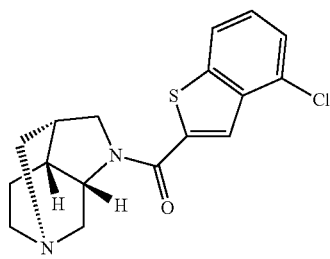 [SMILES: O=C(c1cc2c(Cl)cccc2s1)N1C[C@H]2C[N@]3CC[C@H]2[C@H]1C3]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 0-100% B over 20 minutes, then a 4-minute hold at 100% B; Flow: 25 mL/min. Fractions containing the desired product were combined and dried via centrifugal evaporation. The yield of the product was 12.4 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=3.28 min, M+H=333.08. Proton NMR was acquired in deuterated DMSO. $^1$H NMR (500 MHz, DMSO-$d_6$) δ=8.09-8.00 (m, 1H), 7.93-7.63 (m, 1H), 7.60-7.43 (m, 2H), 4.38-4.17 (m, 1H), 3.98-3.50 (m, 2H), 3.22-3.03 (m, 3H), 2.85-2.61 (m, 4H), 2.44-2.11 (m, 2H), 1.80-1.65 (m, 2H) (signals partially obscured by solvent/water peaks).

EXAMPLE 95: ((3R,3aR,6S,7aS)-hexahydro-3,6-methanopyrrolo[2,3-c]pyridin-1(2H)-yl)(4-methoxy-1H-indazol-3-yl)methanone

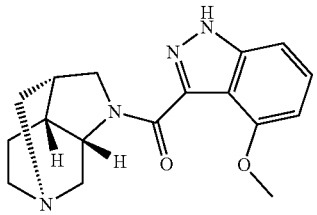 [SMILES: COc1cccc2[nH]nc(C(=O)N3C[C@H]4C[N@]5CC[C@H]4[C@H]3C5)c12]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 20-100% B over 15 minutes, then a 3-minute hold at 100% B; Flow: 20 mL/min. Fractions containing the desired product were combined and dried via centrifugal evaporation. The yield of the product was 3.3 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.18 min, M+H=313.16. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-$d_6$) δ=13.21 (br. s., 1H), 7.42-7.27 (m, 1H), 7.17-7.04 (m, 1H), 6.65-6.53 (m, 1H), 4.20-4.11 (m, 1H), 3.85 (s, 3H), 3.18-2.97 (m, 3H), 2.79-2.59 (m, 4H), 2.45-1.98 (m, 3H), 1.77-1.47 (m, 2H).

EXAMPLE 96: 7-chlorobenzo[b]thiophen-2-yl((3R,3aR,6S,7aS)-hexahydro-3,6-methanopyrrolo[2,3-c]pyridin-1(2H)-yl)methanone

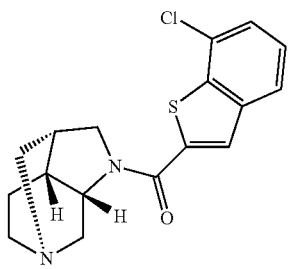 [SMILES: O=C(c1cc2cccc(Cl)c2s1)N1C[C@H]2C[N@]3CC[C@H]2[C@H]1C3]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 0-100% B over 20 minutes, then a 4-minute hold at 100% B; Flow: 25 mL/min. Fractions containing the desired product were combined and dried via centrifugal evaporation. The yield of the product was 13.1 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.92 min, M+H=333.08. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO.

EXAMPLE 97: benzo[d]isothiazol-3-yl((3R,3aR,6S,7aS)-hexahydro-3,6-methanopyrrolo[2,3-c]pyridin-1(2H)-yl)methanone

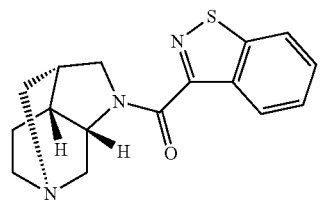 [SMILES: O=C(c1nsc2ccccc12)N1C[C@H]2C[N@]3CC[C@H]2[C@H]1C3]

The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 30-100% B over 13 minutes, then a 3-minute hold at 100% B; Flow: 20 mL/min. Fractions containing the desired product were combined and dried via centrifugal evaporation. The yield of the product was 6.4 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.63 min, M+H=300.11. Proton NMR was acquired in deuterated DMSO. $^1$H NMR (500 MHz, DMSO-$d_6$) δ=8.53-8.41 (m, 1H), 8.36-8.28 (m, 1H), 7.68 (qt, J=1.0, 7.6 Hz, 1H), 7.58 (ddd, J=1.1, 6.9, 8.2 Hz, 1H), 4.35-4.26 (m, 1H), 3.87-3.56 (m, 1H), 3.22-3.14 (m, 2H), 2.89-2.76 (m, 3H), 2.40-2.27 (m, 1H), 2.25-2.16 (m, 1H), 1.83-1.65 (m, 2H).

EXAMPLE 98: (4-chlorophenyl) ((3R,3aR,6S,7aS)-hexahydro-3, 6-methanopyrrolo[2,3-c]pyridin-1 (2H)-yl)methanone

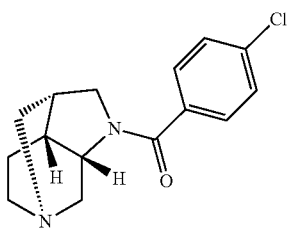 [SMILES: O=C(c1ccc(Cl)cc1)N1C[C@H]2C[N@]3CC[C@H]2[C@H]1C3]

The crude material was purified via preparative LC/MS with the following conditions: Column: Waters XBridge C18, 19×150 mm, 5-µm particles; Guard Column: Waters XBridge C18, 19×10 mm, 5-µm particles; Mobile Phase A: water with 20-mM ammonium acetate; Mobile Phase B: 95:5 methanol:water with 20-mM ammonium acetate; Gradient: 30-100% B over 13 minutes, then a 3-minute hold at 100% B; Flow: 20 mL/min. Fractions containing the desired product were combined and dried via centrifugal evaporation. The yield of the product was 8.8 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.38 min, M+H=277.10. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-d$_6$) δ=7.65-7.57 (m, 1H), 7.55-7.50 (m, 2H), 7.68-7.40 (m, 4H), 4.27-3.67 (m, 1H), 3.62-3.50 (m, 1H), 2.94-2.77 (m, 2H), 2.75-2.64 (m, 1H), 2.38-2.06 (m, 2H), 1.86-1.48 (m, 2H) (some signals obscured by solvent/water peaks).

EXAMPLE 99: benzofuran-2-yl((3R,3aR,6S,7aS)-hexahydro-3,6-methanopyrrolo[2,3-c]pyridin-1(2H)-yl)methanone

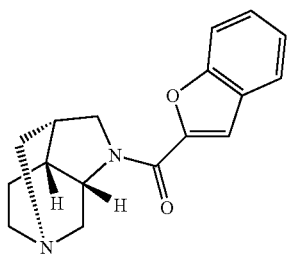

The crude material was purified via preparative LC/MS with the following conditions: Column: Waters XBridge C18, 19×150 mm, 5-µm particles; Guard Column: Waters XBridge C18, 19×10 mm, 5-µm particles; Mobile Phase A: water with 20-mM ammonium acetate; Mobile Phase B: 95:5 methanol:water with 20-mM ammonium acetate; Gradient: 30-100% B over 13 minutes, then a 3-minute hold at 100% B; Flow: 20 mL/min. Fractions containing the desired product were combined and dried via centrifugal evaporation. The yield of the product was 7.2 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.59 min, M+H=283.14. Proton NMR was acquired in deuterated DMSO. $^1$H NMR (500 MHz, DMSO-d$_6$) δ=7.82-7.75 (m, 1H), 7.73-7.66 (m, 1H), 7.60-7.45 (m, 2H), 7.42-7.31 (m, 1H), 4.54-4.21 (m, 1H), 3.96-3.62 (m, 2H), 3.53-3.48 (m, 1H), 3.20-3.13 (m, 1H), 2.94-2.62 (m, 4H), 2.47-2.10 (m, 2H), 1.84-1.71 (m, 2H).

The following examples (100-113) were prepared from (3S,3aS,6R,7aR)-tert-butyl hexahydro-3,6-methanopyrrolo[2,3-c]pyridine-1(2H)-carboxylate according to the method of example 3:

EXAMPLE 100: benzo[b]thiophen-2-yl((3S,3aS,6R,7aR)-hexahydro-3,6-methanopyrrolo[2,3-c]pyridin-1 (2H)-yl)methanone

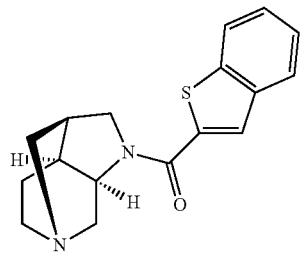

The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 7.0 mg, and its estimated purity by LCMS analysis was 98%. Two analytical LC/MS injections were used to determine the final purity. Injection 1 conditions: Column: Waters BEH C18, 2.0×50 mm, 1.7-µm particles; Mobile Phase A: 5:95 acetonitrile:

water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.56 min, M+H=299.11. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-d$_6$) δ=8.00 (s, 3H), 7.51-7.39 (m, 2H), 4.35-4.12 (m, 1H), 3.97-3.87 (m, 1H), 3.18-2.98 (m, 3H), 2.80-2.54 (m, 4H), 2.40-2.06 (m, 2H), 1.74-1.61 (m, 2H) (some signals obscured by solvent/water peaks).

EXAMPLE 101: ((3S,3aS,6R,7aR)-hexahydro-3,6-methanopyrrolo[2,3-c]pyridin-1(2H)-yl)(1-methyl-1H-indazol-3-yl)methanone

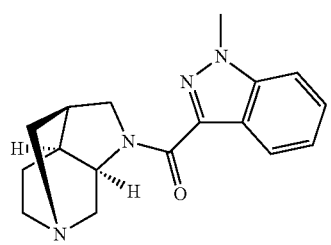

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 6.5 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.40 min, M+H=297.16. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-d$_6$) δ=8.31-8.10 (m, 1H), 7.72 (d, J=8.5 Hz, 1H), 7.48 (d, J=1.2 Hz, 1H), 7.34-7.18 (m, 1H), 4.76-4.19 (m, 1H), 4.13 (d, J=2.4 Hz, 3H), 3.95-3.69 (m, 1H), 3.17-2.99 (m, 3H), 2.82-2.62 (m, 3H), 2.36-2.02 (m, 2H), 1.81-1.57 (m, 2H) (some signals obscured by solvent/water peaks).

EXAMPLE 102: ((3S,3aS,6R,7aR)-hexahydro-3,6-methanopyrrolo[2,3-c]pyridin-1(2H)-yl)(1-methyl-1H-indol-3-yl)methanone

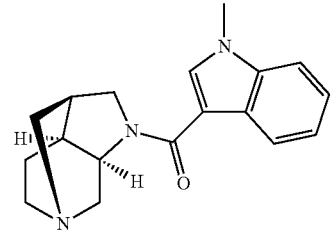 [SMILES: Cn1cc(C(=O)N2C[C@@H]3C[N@@]4CC[C@@H]3[C@@H]2C4)c2ccccc21]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 2.2 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.30 min, M+H=296.17. Proton NMR was acquired in deuterated DMSO. $^1$H NMR (500 MHz, DMSO-d$_6$) δ=8.16 (br. s., 1H), 7.94-7.53 (m, 1H), 7.49 (d, J=8.2 Hz, 1H), 7.24 (ddd, J=1.2, 6.9, 8.0 Hz, 1H), 7.14 (ddd, J=0.9, 7.0, 7.9 Hz, 1H), 4.23-4.09 (m, 1H), 3.86 (s, 3H), 3.18-2.96 (m, 2H), 2.65 (br. s., 3H), 2.35-2.02 (m, 2H), 1.78-1.55 (m, 2H) (some signals obscured by solvent/water peaks).

EXAMPLE 103: ((3S,3aS,6R,7aR)-hexahydro-3,6-methanopyrrolo[2,3-c]pyridin-1(2H)-yl)(5-chloro-1H-indazol-3-yl)methanone

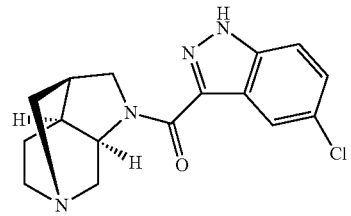 [SMILES: O=C(c1n[nH]c2ccc(Cl)cc12)N1C[C@@H]2C[N@@]3CC[C@@H]2[C@@H]1C3]

The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 4.2 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.70 min, M+H=317.11. Proton NMR was acquired in deuterated DMSO. $^1$H NMR (500 MHz, DMSO-$d_6$) δ=8.26-8.14 (m, 1H), 7.73-7.61 (m, 1H), 7.52-7.37 (m, 1H), 4.76-4.17 (m, 1H), 3.93-3.74 (m, 1H), 3.17-3.02 (m, 3H), 2.68 (t, J=14.0 Hz, 3H), 2.32-2.05 (m, 2H), 1.76-1.61 (m, 2H) (some signals obscured by solvent/water peaks).

EXAMPLE 104: ((3S,3aS,6R,7aR)-hexahydro-3,6-methanopyrrolo[2,3-c]pyridin-1(2H)-yl)(6-methoxy-1H-indazol-3-yl)methanone

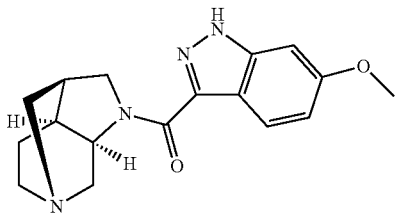 [SMILES: COc1ccc2c(C(=O)N3C[C@@H]4C[N@@]5CC[C@@H]4[C@@H]3C5)n[nH]c2c1]

The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 25 mL/min. Fractions containing the desired product were combined and dried via centrifugal evaporation. The yield of the product was 3.5 mg, and its estimated purity by LCMS analysis was 98%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.31 min, M+H=313.16. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-$d_6$) δ=13.67-12.92 (m, 1H), 8.26-7.79 (m, 1H), 7.00-6.94 (m, 1H), 6.90-6.84 (m, 1H), 4.71-4.19 (m, 1H), 3.84 (s, 4H), 3.15-2.99 (m, 2H), 2.74-2.58 (m, 3H), 2.29-2.03 (m, 2H), 1.73-1.62 (m, 2H).

EXAMPLE 105: ((3S,3aS,6R,7aR)-hexahydro-3,6-methanopyrrolo[2,3-c]pyridin-1(2H)-yl)(5-bromo-1H-indazol-3-yl)methanone

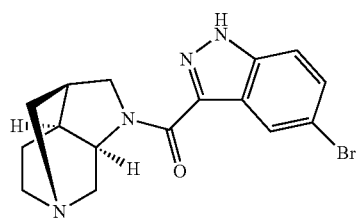

The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 7.0 mg, and its estimated purity by LCMS analysis was 98%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.82 min, M+H=361.06. Proton NMR was acquired in deuterated DMSO. $^1$H NMR (500 MHz, DMSO-$d_6$) δ=8.40-8.34 (m, 1H), 7.65-7.60 (m, 1H), 7.57-7.52 (m, 1H), 4.73-4.20 (m, 1H), 3.90-3.72 (m, 1H), 2.71-2.60 (m, 2H), 2.50-2.43 (m, 1H), 2.28-2.04 (m, 2H), 1.76-1.61 (m, 2H)(some signals obscured by solvent/water peaks).

EXAMPLE 106: 4-chlorobenzo[b]thiophen-2-yl ((3S,3aS,6R,7aR)-hexahydro-3,6-methanopyrrolo[2,3-c]pyridin-1(2H)-yl)methanone

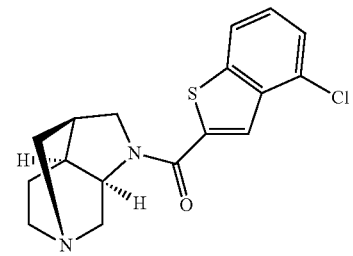 [SMILES: O=C(c1cc2c(Cl)cccc2s1)N1C[C@@H]2C[N@@]3CC[C@@H]2[C@@H]1C3]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 10.1 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.83 min, M+H=333.08. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-$d_6$) δ=8.06-8.01 (m, 1H), 7.92-7.65 (m, 1H), 7.59-7.54 (m, 1H), 7.53-7.45 (m, 1H), 4.33-4.12 (m, 1H), 3.96-3.50 (m, 2H), 3.28 (d, J=11.6 Hz, 4H), 2.73-2.58 (m, 3H), 2.41-2.05 (m, 2H), 1.72-1.62 (m, 2H) (some signals obscured by solvent/water peaks).

EXAMPLE 107: ((3S,3aS,6R,7aR)-hexahydro-3,6-methanopyrrolo[2,3-c]pyridin-1(2H)-yl)(4-methoxy-1H-indazol-3-yl)methanone

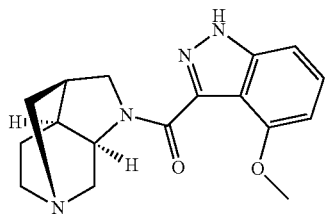 [SMILES: COc1cccc2[nH]nc(C(=O)N3C[C@@H]4C[N@@]5CC[C@@H]4[C@@H]3C5)c12]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 7.0 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.08 min, M+H=313.16. Proton NMR was acquired in deuterated DMSO. $^1$H NMR (500 MHz, DMSO-$d_6$) δ=13.31-13.10 (m, 1H), 7.36-7.27 (m, 1H), 7.15-7.08 (m, 1H), 6.65-6.55 (m, 1H), 3.88-3.82 (m, 3H), 4.25-3.54 (m, 1H), 3.19-2.97 (m, 1H), 2.60 (s, 2H), 2.45 (s, 1H), 2.30-2.17 (m, 1H), 2.12-1.98 (m, 2H), 1.75-1.43 (m, 2H) (some signals obscured by solvent/water peaks).

EXAMPLE 108: 7-chlorobenzo[b]thiophen-2-yl ((3S,3aS,6R,7aR)-hexahydro-3,6-methanopyrrolo[2,3-c]pyridin-1(2H)-yl)methanone

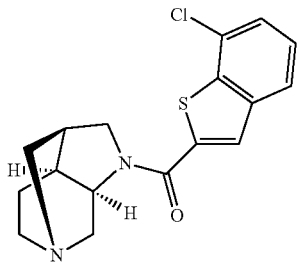 [SMILES: O=C(c1cc2cccc(Cl)c2s1)N1C[C@@H]2C[N@@]3CC[C@@H]2[C@@H]1C3]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 8.7 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.87 min, M+H=333.08. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-$d_6$) δ=8.18-7.79 (m, 2H), 7.61 (d, J=7.6 Hz, 1H), 7.55-7.46 (m, 1H), 4.34-4.13 (m, 1H), 3.95-3.49 (m, 2H), 3.17-2.97 (m, 2H), 2.78-2.56 (m, 4H), 2.41-2.04 (m, 2H), 1.76-1.59 (m, 2H) (some signals obscured by solvent/water peaks).

EXAMPLE 109: ((3S,3aS,6R,7aR)-hexahydro-3,6-methanopyrrolo[2,3-c]pyridin-1(2H)-yl)(6-chloro-1H-indazol-3-yl)methanone

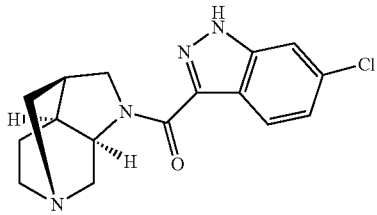 [SMILES: O=C(c1n[nH]c2cc(Cl)ccc12)N1C[C@@H]2C[N@@]3CC[C@@H]2[C@@H]1C3]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 7.0 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.52 min, M+H=317.11. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-d$_6$) δ=8.24-8.14 (m, 1H), 7.73-7.68 (m, 1H), 7.26 (td, J=1.5, 8.5 Hz, 1H), 4.71-4.17 (m, 1H), 3.92-3.73 (m, 1H), 3.15-3.02 (m, 2H), 2.73-2.61 (m, 3H), 2.35-2.04 (m, 2H), 1.75-1.61 (m, 2H) (some signals obscured by solvent/water peaks).

EXAMPLE 110: ((3S,3aS,6R,7aR)-hexahydro-3,6-methanopyrrolo[2,3-c]pyridin-1(2H)-yl)(5-methoxy-1H-indazol-3-yl)methanone

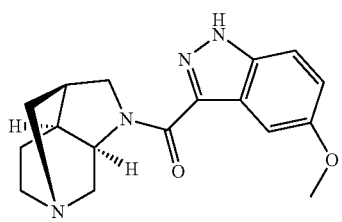 [SMILES: COc1ccc2[nH]nc(C(=O)N3C[C@@H]4C[N@@]5CC[C@@H]4[C@@H]3C5)c2c1]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 6.9 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=1.76 min, M+H=313.16. Proton NMR was acquired in deuterated DMSO.

EXAMPLE 111: benzo[d]isothiazol-3-yl((3S,3aS,6R,7aR)-hexahydro-3,6-methanopyrrolo[2,3-c]pyridin-1(2H)-yl)methanone

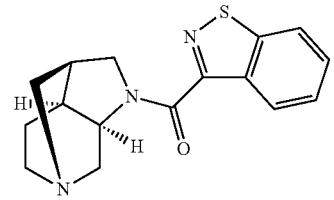 [SMILES: O=C(c1nsc2ccccc12)N1C[C@@H]2C[N@@]3CC[C@@H]2[C@@H]1C3]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 7.9 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.46 min, M+H=300.11. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-d$_6$) δ=8.41 (t, J=8.5 Hz, 1H), 8.30 (d, J=7.9 Hz, 1H), 7.67 (t, J=7.5 Hz, 1H), 7.58 (d, J=7.3 Hz, 1H), 4.29-4.11 (m, 1H), 3.86-3.52 (m, 2H), 3.07 (d, J=12.8 Hz, 3H), 2.81-2.60 (m, 4H), 2.47-2.07 (m, 3H), 1.74-1.53 (m, 2H) (some signals obscured by solvent/water peaks).

EXAMPLE 112: (4-chlorophenyl)((3S,3aS,6R,7aR)-hexahydro-3,6-methanopyrrolo[2,3-c]pyridin-1(2H)-yl)methanone

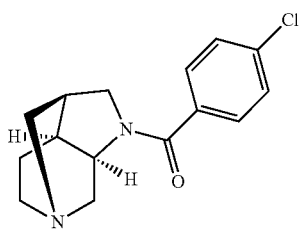 [SMILES: O=C(c1ccc(Cl)cc1)N1C[C@@H]2C[N@@]3CC[C@@H]2[C@@H]1C3]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 7.8 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.36 min, M+H=277.10. Proton NMR was acquired in deuterated DMSO. $^1$H NMR (500 MHz, DMSO-$d_6$) δ=7.61-7.42 (m, 4H), 4.12-3.60 (m, 1H), 3.54-3.47 (m, 1H), 3.23-2.85 (m, 4H), 2.72-2.58 (m, 3H), 2.45-2.36 (m, 1H), 2.27-2.00 (m, 2H), 1.68-1.44 (m, 2H) (some signals obscured by solvent/water peaks).

EXAMPLE 113: benzofuran-2-yl((3S,3aS,6R,7aR)-hexahydro-3,6-methanopyrrolo[2,3-c]pyridin-1(2H)-yl)methanone

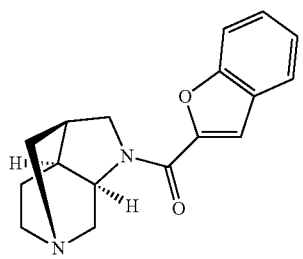 [SMILES: O=C(c1cc2ccccc2o1)N1C[C@@H]2C[N@@]3CC[C@@H]2[C@@H]1C3]

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-95% B over 25 minutes, then a 4-minute hold at 95% B; Flow: 20 mL/min. Fractions containing the desired product were combined and dried via centrifugal evaporation. The yield of the product was 9.8 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.55 min, M+H=283.14. Proton NMR was acquired in deuterated DMSO. $^1$H NMR (500 MHz, DMSO-$d_6$) δ=7.84-7.74 (m, 1H), 7.72-7.64 (m, 1H), 7.60-7.44 (m, 2H), 7.39-7.32 (m, 1H), 4.42-4.14 (m, 1H), 3.93-3.58 (m, 1H), 3.18-2.96 (m, 2H), 2.77-2.58 (m, 3H), 2.36-1.97 (m, 2H), 1.74-1.61 (m, 3H) (some signals obscured by solvent/water peaks).

EXAMPLE 114

(hexahydro-1H-1,6-methanopyrrolo[3,4-d]azepin-2(7H)-yl)(1H-indazol-3-yl)methanone

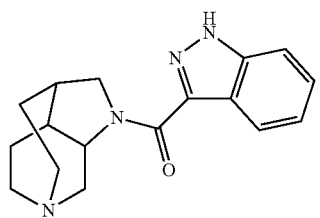 [SMILES: O=C(c1n[nH]c2ccccc12)N1CC2CCN3CCC2C1C3]

Step A: 2-(2-(triethylsilyl)-1H-pyrrolo[2,3-c]pyridin-3-yl)ethanol

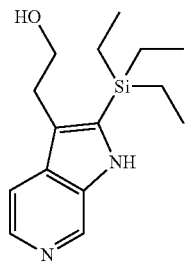 [SMILES: CC[Si](CC)(CC)c1[nH]c2cnccc2c1CCO]

A resealable pressure tube was charged with 4-iodopyridin-3-amine (2.4 g, 10.9 mmol), 4-(triethylsilyl)but-3-yn-ol (5.0 g, 27.3 mmol), lithium chloride (0.46 g, 42.0 mmol), sodium carbonate (2.31 g, 21.8 mmol) and 1,1'-bis(diphenylphosphino)ferrocenopalladium(II) dichloride, toluene (0.45 g, 0.55 mmol), the tube was sealed and heated on a 100° C. oil bath for ~20 h. The reaction mixture was cooled to ambient temperature, diluted with EtOAc (75 mL) and ether (75 mL). Water (150 mL) was added and the biphasic mixture was filtered through celite. The filtrate was transferred to a separatory funnel and the phases were separated and the aqueous fraction extracted twice more with ethyl acetate. The combined organic layers were washed with water and brine, dried over sodium sulfate, filtered and evaporated. The crude was purified by silica gel chromatography, eluting with 2-20% (9:1 MeOH/NH$_4$OH)/chloroform, affording 2-(2-(triethylsilyl)-1H-pyrrolo[2,3-c]pyridin-3-yl)ethanol (2.45 g, 81% yield). LCMS method A: retention time=3.44 min, M+H=277.25. $^1$H NMR (400 MHz, CHLOROFORM-d) δ=8.79 (s, 1H), 8.65-8.47 (m, 1H), 8.22 (d, J=5.5 Hz, 1H), 7.56 (d, J=5.3 Hz, 1H), 3.91 (t, J=6.9 Hz, 2H), 3.13 (t, J=6.9 Hz, 2H), 1.82 (br. s, 1H), 1.12-0.90 (m, 15H).

Step B: 2-(1H-pyrrolo[2,3-c]pyridin-3-yl)ethanol

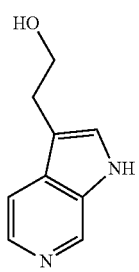 [SMILES: OCCc1c[nH]c2cnccc12]

A flask was charged with 2-(2-(triethylsilyl)-1H-pyrrolo[2,3-c]pyridin-3-yl)ethanol (2.45 g, 8.9 mmol), THF (5 mL) and TBAF (11 mL of a 1.0M solution in THF, 11 mmol). The reaction mixture was allowed to react overnight. After reacting overnight, conversion was low, so the entire mixture was transferred to a pressure vessel and heated on a 100° C. oil bath for 1.5 h. The mixture was cooled to ambient temperature, the solvent was evaporated and the crude was purified by silica gel chromatography, eluting with 5-40% (9:1 MeOH/NH$_4$OH)/chloroform, affording 2-(1H-pyrrolo[2,3-c]pyridin-3-yl)ethanol (2.5 g, ~55% pure, ~96% yield), which still contained some residual TBAF, but was taken forward to the next step as-is. $^1$H NMR (400 MHz, CHLOROFORM-d) δ=8.59 (s, 1H), 7.97 (d, J=5.5 Hz, 1H), 7.39-7.32 (m, 2H), 3.88 (s, 2H), 2.97 (t, J=6.4 Hz, 2H) (peaks believed to be due to TBAF not reported).

Step C: 3-(2-((triisopropylsilyl)oxy)ethyl)-1H-pyrrolo[2,3-c]pyridine

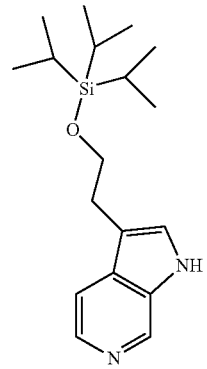 [SMILES: CC(C)[Si](OCCc1c[nH]c2cnccc12)(C(C)C)C(C)C]

A flask was charged with 2-(1H-pyrrolo[2,3-c]pyridin-3-yl)ethanol (2.5 g, ~55% pure, 8.5 mmol), TIPSCl (3.6 mL, 17.0 mmol) and imidazole (1.15 g, 17.0 mmol). The mixture was allowed to age for 1.5 h, then poured into a 1:1 mixture of ether/EtOAc and washed with water 3×. The combined organics were dried over sodium sulfate, filtered and evaporated. The crude was purified by silica gel chromatography eluting with a gradient from 10-100% EtOAc/hexanes., affording 3-(2-((triisopropylsilyl)oxy)ethyl)-1H-pyrrolo[2,3-c]pyridine (1.47 g, 54.4% yield). $^1$H NMR (400 MHz, CHLOROFORM-d) δ=8.80 (d, J=0.8 Hz, 1H), 8.28 (d, J=5.5 Hz, 1H), 7.55 (d, J=5.5 Hz, 1H), 3.96 (t, J=7.0 Hz, 2H), 3.03 (s, 2H), 1.19-0.96 (m, 21H) (one peak from the aromatic portion is missing from the spectrum, possibly obscured by the solvent peak).

Step D: tert-butyl 3-(2-((triisopropylsilyl)oxy)ethyl)-1H-pyrrolo[2,3-c]pyridine-1-carboxylate

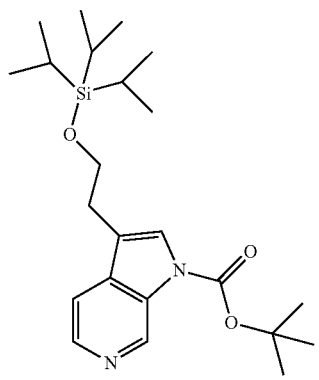 [SMILES: CC(C)[Si](OCCc1cn(C(=O)OC(C)(C)C)c2cnccc12)(C(C)C)C(C)C]

A flask was charged with 3-(2-((triisopropylsilyl)oxy)ethyl)-1H-pyrrolo[2,3-c]pyridine (1.47 g, 4.6 mmol), di-tert-butyldicarbonate (1.2 g, 5.5 mmol), triethylamine (0.97 mL, 6.9 mmol) and DCM (25 mL). The mixture was allowed to age for 30 min, then evaporated and purified by silica gel chromatography, eluting with 0-50% EtOAc in hexanes, affording tert-butyl 3-(2-((triisopropylsilyl)oxy)ethyl)-1H-pyrrolo[2,3-c]pyridine-1-carboxylate (1.3 g, 67% yield). $^1$H NMR (500 MHz, CHLOROFORM-d) δ=9.48-9.26 (m, 1H), 8.43 (d, J=5.5 Hz, 1H), 7.63 (s, 1H), 7.54-7.45 (m, 1H), 3.97 (t, J=6.6 Hz, 2H), 2.94 (t, J=6.6 Hz, 2H), 1.71 (s, 9H), 1.19-1.05 (m, 21H).

Step E: tert-butyl 3-(2-((triisopropylsilyl)oxy)ethyl) octahydro-1H-pyrrolo[2,3-c]pyridine-1-carboxylate

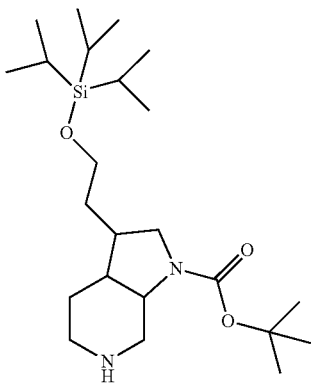 [SMILES: CC(C)[Si](OCCC1CN(C(=O)OC(C)(C)C)C2CNCCC12)(C(C)C)C(C)C]

A Parr bottle was charged with platinum oxide (0.200 g, 0.88 mmol) and a solution of tert-butyl 3-(2-((triisopropylsilyl)oxy)ethyl)-1H-pyrrolo[2,3-c]pyridine-1-carboxylate (1.3 g, 3.11 mmol) in ethanol (20 mL) and acetic acid (5 mL) was added. The mixture was hydrogenated on a Parr apparatus overnight. After reacting overnight, LCMS and TLC show complete conversion. The mixture was filtered through celite and the filtrate evaporated. The residue was partitioned between sodium bicarbonate and chloroform and the mixture was extracted thrice with chloroform, dried over sodium sulfate, filtered, and evaporated to afford tert-butyl 3-(2-((triisopropylsilyl)oxy)ethyl)octahydro-1H-pyrrolo[2,3-c]pyridine-1-carboxylate (1.32 g, 100% yield assumed for purpose of calculating stoichiometry in next step).

Step F: 6-benzyl 1-tert-butyl 3-(2-((triisopropylsilyl)oxy)ethyl)hexahydro-1H-pyrrolo[2,3-c]pyridine-1,6(2H)-dicarboxylate

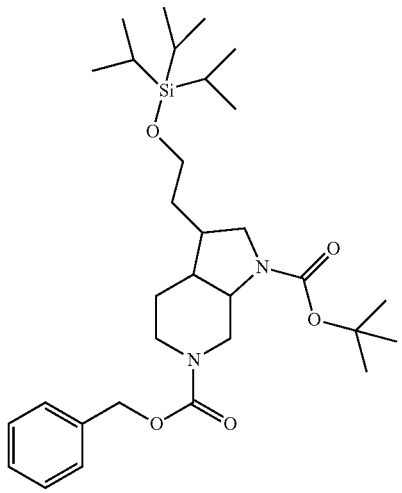

A flask was charged with tert-butyl 3-(2-((triisopropylsilyl)oxy)ethyl)octahydro-1H-pyrrolo[2,3-c]pyridine-1-carboxylate (1.32 g, 3.11 mmol), THF (15 mL) and a 10% aq. solution of sodium carbonate (15 mL, 14.2 mmol) and CBz-Cl (0.7 mL, 4.9 mmol) was added. The mixture was stirred at rt for 30 min, the mixture was diluted with chloroform and the phases separated. The aqueous phase was extracted 3× more with chloroform, dried over sodium sulfate, filtered and evaporated, and the crude residue purified by silica gel chromatography, eluting with a gradient from 0-25% EtOAc in hexanes, to afford 6-benzyl 1-tert-butyl 3-(2-((triisopropylsilyl)oxy)ethyl)hexahydro-1H-pyrrolo[2,3-c]pyridine-1,6(2H)-dicarboxylate (1.59 g, 92% yield). LCMS method A: retention time=3.10 min, M+H-Boc=461.4.

Step G: 6-benzyl 1-tert-butyl 3-(2-((triisopropylsilyl)oxy)ethyl)hexahydro-1H-pyrrolo[2,3-c]pyridine-1,6(2H)-dicarboxylate

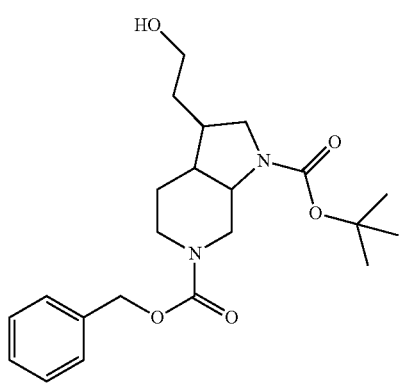 [SMILES: CC(C)(C)OC(=O)N1CC(CCO)C2CCN(C(=O)OCc3ccccc3)CC21]

A flask was charged with 6-benzyl 1-tert-butyl 3-(2-((triisopropylsilyl)oxy)ethyl)hexahydro-1H-pyrrolo[2,3-c]pyridine-1,6(2H)-dicarboxylate (1.59 g, 2.84 mmol), THF (25 mL) and TBAF (3 mL of a 1.0M solution in THF, 3.0 mmol). The mixture was allowed to age for 2 h, poured into water and extracted 3× with chloroform. The combined organics were dried over sodium sulfate, filtered and evaporated, and the crude material was purified by silica gel chromatography, eluting with a gradient from 15-100% EtOAc in hexanes, affording 6-benzyl 1-tert-butyl 3-(2-((triisopropylsilyl)oxy)ethyl)hexahydro-1H-pyrrolo[2,3-c]pyridine-1,6(2H)-dicarboxylate (1.02 g, 89% yield). LMCS Method A: retention time=3.82 min, M+H-Boc=305.25.

Step H: 6-benzyl 1-tert-butyl 3-(2-chloroethyl)hexahydro-1H-pyrrolo[2,3-c]pyridine-1,6(2H)-dicarboxylate and 6-benzyl 1-tert-butyl 3-(2-(tosyloxy)ethyl)hexahydro-1H-pyrrolo[2,3-c]pyridine-1,6(2H)-dicarboxylate

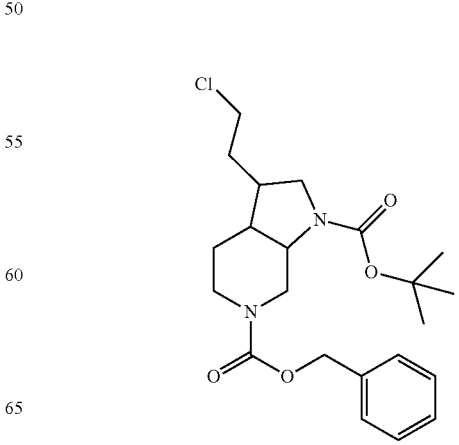

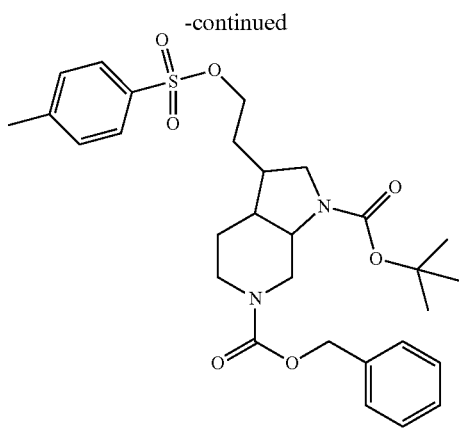

A flask was charged with 6-benzyl 1-tert-butyl 3-(2-((triisopropylsilyl)oxy)ethyl)hexahydro-1H-pyrrolo[2,3-c]pyridine-1,6(2H)-dicarboxylate (1.02 g, 2.52 mmol) and pyridine (6.3 mL) and cooled on an ice bath. To this mixture was added tosyl chloride (0.73 g, 3.83 mmol) and the ice bath was removed and the mixture was allowed to age overnight. Some of the pyridine was evaporated on the rotovap, and the mixture was poured into a mixture of 1N HCl and chloroform. The phases were separated and the aqueous was extracted twice more with chloroform. The combine organics were washed with sodium bicarbonate solution, followed by brine, and the organics were dried over sodium sulfate, filtered and evaporated. The residue was purified by silica gel chromatography, eluting with a gradient from 1-100% EtOAc in hexanes. Two components were collected: The first peak to elute was 6-benzyl 1-tert-butyl 3-(2-chloroethyl)hexahydro-1H-pyrrolo[2,3-c]pyridine-1,6(2H)-dicarboxylate (0.35 g, 33% yield) LCMS method A: retention time=4.09 min, M+H-Boc=323.2. The second peak to elute was 6-benzyl 1-tert-butyl 3-(2-(tosyloxy)ethyl)hexahydro-1H-pyrrolo[2,3-c]pyridine-1,6(2H)-dicarboxylate (0.25 g, 18% yield) LCMS method A: retention time=4.07 min, M+H-Boc=459.3.

In an alternate method, 6-benzyl 1-tert-butyl 3-(2-(tosyloxy)ethyl)hexahydro-1H-pyrrolo[2,3-c]pyridine-1,6(2H)-dicarboxylate was also prepared by the following sequence:

Step I: 3-(2-(benzyloxy)ethyl)-2-(trimethylsilyl)-1H-pyrrolo[2,3-c]pyridine

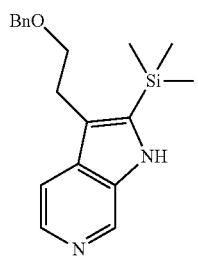 [SMILES: C[Si](C)(C)c1[nH]c2cnccc2c1CCOCc1ccccc1]

A resealable pressure tube was charged with 4-iodopyridin-3-amine (2.3 g, 10.5 mmol), (4-(benzyloxy)but-1-yn-1-yl)trimethylsilane (6.1 g, 26.1 mmol), lithium chloride (0.44 g, 10.5 mmol), sodium carbonate (2.21 g, 20.9 mmol) and 1,1'-bis(diphenylphosphino)ferrocenopalladium(II) dichloride, toluene (0.43 g, 0.52 mmol), the tube was sealed and heated on a 100° C. oil bath for ~20 h. The reaction mixture was cooled to ambient temperature, diluted with EtOAc (75 mL) and ether (75 mL). Water (150 mL) was added and the biphasic mixture was filtered through celite. The filtrate was transferred to a separatory funnel and the phases were separated and the aqueous fraction extracted twice more with ethyl acetate. The combined organic layers were washed with water and brine, dried over sodium sulfate, filtered and evaporated. The crude was purified by silica gel chromatography, eluting with 5-20% (9:1 MeOH/NH$_4$OH)/chloroform, affording 3-(2-(benzyloxy)ethyl)-2-(trimethylsilyl)-1H-pyrrolo[2,3-c]pyridine, as a mixture with some of the de-silylated regioisomer (4 g, 118% yield, contains some residual DMF). LCMS method A: retention time of major component=4.08 min, M+H=325.5. The mixture was dissolved in THF (100 mL) and treated with TBAF (12.3 mL of a 1.0M solution in THF, 12.3 mmol) at room temperature for ~1 h. No change was observed by TLC. The mixture was evaporated and re-purified by silica gel chromatography under the same conditions as before to afford 3-(2-(benzyloxy)ethyl)-2-(trimethylsilyl)-1H-pyrrolo[2,3-c]pyridine, essentially free of the regioisomer (2.5 g, 63% yield). $^1$H NMR (400 MHz, CHLOROFORM-d) δ=8.80 (s, 1H), 8.44-8.32 (m, 1H), 8.22 (d, J=5.5 Hz, 1H), 7.58-7.47 (m, 1H), 7.41-7.30 (m, 5H), 4.56 (s, 2H), 3.69 (t, J=7.7 Hz, 2H), 3.18 (t, J=7.7 Hz, 2H), 0.42 (s, 9H).

Step J: tert-butyl 3-(2-(benzyloxy)ethyl)-1H-pyrrolo[2,3-c]pyridine-1-carboxylate

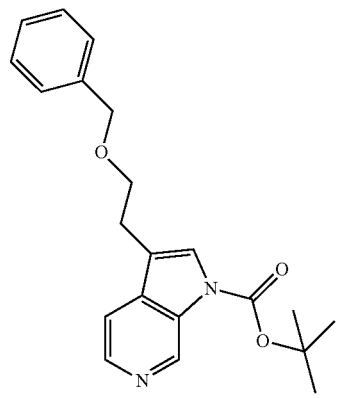 [SMILES: CC(C)(C)OC(=O)n1cc(CCOCc2ccccc2)c2ccncc21]

A flask was charged with 3-(2-(benzyloxy)ethyl)-2-(trimethylsilyl)-1H-pyrrolo[2,3-c]pyridine (2.5 g, 7.7 mmol) and a solution of TBAF in THF (8 mL, 8 mmol). The mixture was allowed to age overnight, evaporated and purified by silica gel chromatography (5-40% (9:1 MeOH/NH$_4$OH)/chloroform), affording the deprotected product contaminated with TBAF (2.2 g). The residue was dissolved in DCM (44 mL) and TEA (2.4 mL, 17.4 mmol) and di-tert-butyl-dicarbonate (2.85 g, 13.1 mmol) were added. The mixture was stirred for 30 min, evaporated and purified by silica gel chromatography, eluting with a gradient from 10-100% EtOAc in hexanes to afford tert-butyl 3-(2-(benzyloxy)ethyl)-1H-pyrrolo[2,3-c]pyridine-1-carboxylate (1.38 g, 45% yield). $^1$H NMR (400 MHz, CHLOROFORM-d) δ=9.47-9.27 (m, 1H), 8.41 (d, J=5.5 Hz, 1H), 7.61 (s, 1H), 7.48 (dd, J=1.0, 5.3 Hz, 1H), 7.39-7.30 (m, 5H), 4.57 (s, 2H), 3.78 (t, J=6.7 Hz, 2H), 3.08-2.98 (m, 2H), 1.71 (s, 9H) (HNMR also shows ethyl acetate present).

Step K: tert-butyl 3-(2-hydroxyethyl)octahydro-1H-pyrrolo[2,3-c]pyridine-1-carboxylate, AcOH

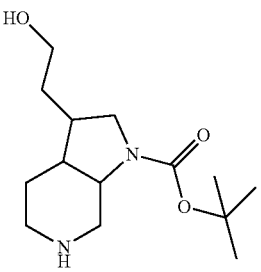

A Parr bottle was charged with 20% palladium hydroxide on carbon (0.3 g), and a solution of tert-butyl 3-(2-(benzyloxy)ethyl)-1H-pyrrolo[2,3-c]pyridine-1-carboxylate (1.38 g, 3.92 mmol) in EtOH (50 mL) was added. The mixture was treated with 55 psi hydrogen and shaken overnight. After reacting overnight, the mixture was flushed with nitrogen and charged with an additional portion of 20% palladium hydroxide on carbon (0.3 g) in acetic acid (10 mL). The mixture was again hydrogenated at the same pressure for 3d. After 3d, the mixture was flushed with nitrogen and filtered through celite, eluting with EtOH. The residue was evaporated to afford tert-butyl 3-(2-hydroxyethyl)octahydro-1H-pyrrolo[2,3-c]pyridine-1-carboxylate, AcOH, yield was assumed to be quantitative for the purpose of calculating stoichiometry for the next step. LCMS showed two peaks with the target mass, possibly diastereomers: LCMS method A: peak 1 retention time=1.90 min, M+H=271.25, peak 2 retention time=2.08 min, M+H=271.3. The mixture was taken on to the next step without further purification.

Step L: 6-benzyl 1-tert-butyl 3-(2-(tosyloxy)ethyl) hexahydro-1H-pyrrolo[2,3-c]pyridine-1,6(2H)-dicarboxylate

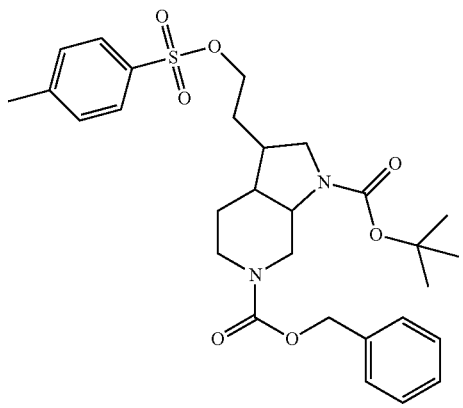 [SMILES: Cc1ccc(S(=O)(=O)OCCC2CN(C(=O)OC(C)(C)C)C3CN(C(=O)OCc4ccccc4)CCC23)cc1]

A flask was charged with tert-butyl 3-(2-hydroxyethyl) octahydro-1H-pyrrolo[2,3-c]pyridine-1-carboxylate, AcOH (1.3 g, 3.9 mmol), THF (20 mL), 10% aq. potassium carbonate (20 mL) and CBz-Cl (0.84 mL, 5.9 mmol). The mixture as stirred at ambient temperature for 1 h, diluted with chloroform and the phases were separated. The aqueous was extracted thrice more with chloroform and dried over sodium sulfate, filtered and evaporated. The residue was purified by silica gel chromatography, eluting with 10-100% EtOAc in hexanes. The fractions containing product were evaporated to give a clear oil (1.32 g) which was redissolved in DCM (8 mL). Pyridine (8 mL) was added, the solution was cooled on an ice bath and tosyl chloride (0.7 g, 3.67 mmol) was added. The mixture was stirred at ambient temperature overnight. Some of the pyridine was evaporated and the mixture partitioned between 1N HCl and chloroform. The mixture was extracted 3× with chloroform, washed with sodium bicarbonate solution and brine, and dried over sodium sulfate, filtered and evaporated. The residue was purified by silica gel chromatography eluting with 1-100% EtOAc/hexanes to afford 6-benzyl 1-tert-butyl 3-(2-(tosyloxy)ethyl)hexahydro-1H-pyrrolo[2,3-c]pyridine-1,6(2H)-dicarboxylate (1.3 g, 2.3 mmol, 71% yield). LCMS method A: retention time=4.2 min, M+H-Boc=459.25.

Step M: tert-butyl hexahydro-1H-1,6-methanopyrrolo[3,4-d]azepine-2(7H)-carboxylate

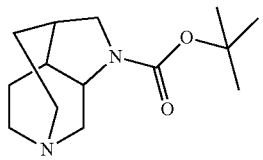 [SMILES: CC(C)(C)OC(=O)N1CC2CCN3CCC2C1C3]

A Parr bottle was charged with 10% palladium on carbon (0.45 g) and a solution of 6-benzyl 1-tert-butyl 3-(2-(tosyloxy)ethyl)hexahydro-1H-pyrrolo[2,3-c]pyridine-1,6(2H)-dicarboxylate (1.3 g, 2.3 mmol) in EtOH (50 mL) was added. The mixture was hydrogenated on a Parr shaker at 55 psi for 2 h. The mixture was flushed with nitrogen, filtered through celite to remove the catalyst, eluting with EtOH to give a final volume of ~250 mL. To this solution was added potassium carbonate (1 g) and the mixture was heated at 60° C. overnight. The mixture was cooled to ambient temperature, filtered to remove solids, and evaporated. The residue was evaporated onto silica gel from methanol and purified by silica gel chromatography, eluting with 5-20% (10% NH4OH/MeOH) in chloroform to afford tert-butyl hexahydro-1H-1,6-methanopyrrolo[3,4-d]azepine-2(7H)-carboxylate (185 mg, 32% yield) along with some mixed fractions. $^1$H NMR (400 MHz, CHLOROFORM-d) δ=4.02-3.77 (m, 1H), 3.68-3.40 (m, 1H), 3.33-3.08 (m, 2H), 3.08-2.79 (m, 4H), 2.69-2.40 (m, 2H), 2.09-1.62 (m, 5H), 1.59-1.44 (m, 10H) (HNMR complicated by rotomers, integration shows one more proton than expected).

6-benzyl 1-tert-butyl 3-(2-chloroethyl)hexahydro-1H-pyrrolo[2,3-c]pyridine-1,6(2H)-dicarboxylate was also converted to tert-butyl hexahydro-1H-1,6-methanopyrrolo[3,4-d]azepine-2(7H)-carboxylate using this procedure, with the modification that heating was at 90° C. for 2 h instead of 60° C. overnight.

Step N: (hexahydro-1H-1,6-methanopyrrolo[3,4-d]azepin-2(7H)-yl)(1H-indazol-3-yl)methanone

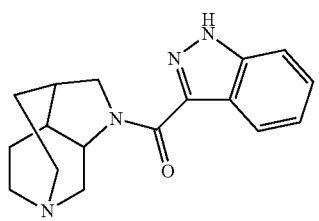 [SMILES: O=C(c1n[nH]c2ccccc12)N1CC2CCN3CCC2C1C3]

tert-butyl hexahydro-1H-1,6-methanopyrrolo[3,4-d]azepine-2(7H)-carboxylate (50 mg, 0.2 mmol) and 1H-indazole-3-carboxylic acid (40 mg, 0.25 mmol) were reacted according to the method of example 1, step D to afford (hexahydro-1H-1,6-methanopyrrolo[3,4-d]azepin-2(7H)-yl)(1H-indazol-3-yl)methanone (49 mg, 79% yield). LCMS method A: retention time=2.13 min, M+H=297.25. $^1$H NMR (400 MHz, CHLOROFORM-d) δ=12.81-10.11 (m, 1H), 8.43 (dd, J=0.9, 8.2 Hz, 1H), 7.58-7.37 (m, 2H), 7.36-7.29 (m, 1H), 5.07-4.48 (m, 1H), 4.30-4.08 (m, 1H), 3.70-2.63 (m, 9H), 2.26-1.98 (m, 2H), 1.94-1.62 (m, 6H) (integration is complicated by rotamers and some signals are obscured by the water and solvent peaks, integration affords more protons than theoretical).

EXAMPLE 115

1,4-diazaadamantan-4-yl(1H-indazol-3-yl)methanone

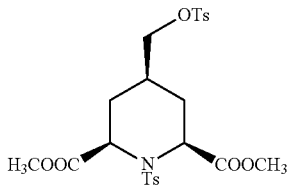

Step A: (2R,4s,6S)-dimethyl 1-tosyl-4-((tosyloxy)methyl)piperidine-2,6-dicarboxylate

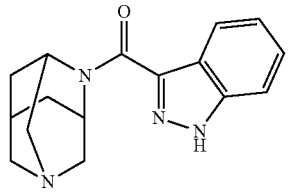 [SMILES: O=C(c1n[nH]c2ccccc12)N1C2CC3CC1CN(C3)C2]

Dimethyl 4-(hydroxymethyl)piperidine-2,6-dicarboxylate (4.5 g, 14.59 mmol) was dissolved in pyridine (15 ml) and TsCl (6.96 g, 36.5 mmol) was added. The mixture was stirred at rt for 2 h. The mixture was partitioned between EtOAc and 1N HCl and washed 3× with 1N HCl. The combined organics were washed with aq. sodium bicarbonate and dried over sodium sulfate, filtered, and evaporated. The crude material was purified by silica gel chromatography using a gradient of 20-100% EtOAc/Hex on 80 g column to afford dimethyl 1-tosyl-4-((tosyloxy)methyl)piperidine-2,6-dicarboxylate (5.0 g, 9.27 mmol, 63.5% yield) $^1$H NMR (400 MHz, CHLOROFORM-d) δ=7.85-7.73 (m, 4H), 7.34 (d, J=8.0 Hz, 2H), 7.37 (d, J=8.0 Hz, 2H), 4.50 (t, J=7.2 Hz, 2H), 3.87 (d, J=6.0 Hz, 2H), 3.67 (s, 6H), 2.48 (s, 3H), 2.46 (s, 3H), 2.06-1.97 (m, 2H), 1.69 (dd, J=6.5, 12.5 Hz, 3H).

Step B: (2R,4s,6S)-dimethyl 4-(azidomethyl)-1-tosylpiperidine-2, 6-dicarboxylate

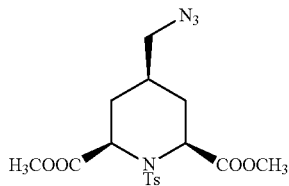

A resealable pressure vessel was charged with 1-tosyl-4-((tosyloxy)methyl)piperidine-2,6-dicarboxylate (5.0 g, 9.27 mmol, 63.5% yield), DMF (10 mL) and sodium azide (1.84 g, 28.4 mmol). The vessel was sealed and heated on a 80° C. oil bath for 90 min. The mixture was cooled to rt, diluted with ethyl acetate, washed with saturated aq. sodium bicarbonate thrice, followed by water and brine. The organics were dried over sodium sulfate, filtered and evaporated. HNMR showed small amounts of DMF and EtOAc present, and the material was used without further purification: dimethyl 4-(azidomethyl)-1-tosylpiperidine-2,6-dicarboxylate (3.73 g, 9.09 mmol, 96% yield) LCMS Method A: retention time=3.70 min, M+H=433.2. $^1$H NMR (500 MHz, CHLOROFORM-d) δ=7.85-7.80 (m, 2H), 7.35 (d, J=8.0 Hz, 2H), 4.54 (t, J=7.4 Hz, 2H), 3.70 (s, 6H), 3.25 (d, J=6.8 Hz, 2H), 2.46 (s, 3H), 2.13-2.04 (m, 2H), 1.75 (ddd, J=6.9, 10.6, 13.9 Hz, 2H), 1.61-1.50 (m, 1H)(some signals partially obscured by water peak).

Step C: ((2R,4s,6S)-4-(azidomethyl)-1-tosylpiperidine-2,6-diyl)dimethanol

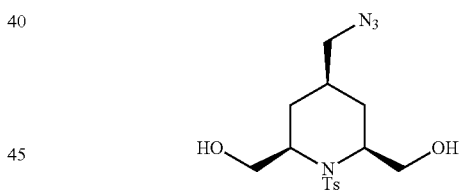

Dimethyl 4-(azidomethyl)-1-tosylpiperidine-2,6-dicarboxylate (3.73 g, 9.09 mmol) was dissolved in THF (91 ml) and LiBH$_4$ (9.09 ml, 18.18 mmol) was added. The mixture was allowed to react overnight and then quenched with ~8 ml 1N HCl. After stirring ~10 min, the mixture was partitioned between chloroform and water. The phases were separated and the aqueous fraction was extracted twice more with chloroform, washed with saturated aq. sodium bicarbonate, dried over sodium sulfate, filtered and evaporated to afford ((2R,4s,6S)-4-(azidomethyl)-1-tosylpiperidine-2,6-diyl)dimethanol (2.71 g, 7.65 mmol, 84% yield), which contained a small amount of THF by HNMR, but was taken forward without further purification. LCMS Method A: retention time=3.32 min, M+H=355.15. $^1$H NMR (400 MHz, CHLOROFORM-d) δ=7.76 (d, J=8.3 Hz, 2H), 7.36 (d, J=8.0 Hz, 2H), 4.11-4.01 (m, 2H), 3.86 (dd, J=4.5, 11.5 Hz, 2H), 3.56 (dd, J=6.5, 11.5 Hz, 2H), 3.02 (d, J=6.5 Hz, 2H), 2.46 (s, 3H), 1.81-1.67 (m, 2H), 1.21-1.10 (m, 2H), 0.93-0.74 (m, 1H).

Step D: ((2R,4s,6S)-4-(azidomethyl)-1-tosylpiperidine-2,6-diyl)bis(methylene)bis(4-methylbenzenesulfonate)

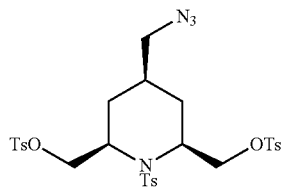 [SMILES: Cc1ccc(S(=O)(=O)OC[C@@H]2C[C@H](CN=[N+]=[N-])C[C@H](COS(=O)(=O)c3ccc(C)cc3)N2S(=O)(=O)c2ccc(C)cc2)cc1]

To a solution of ((2R,4s,6S)-4-(azidomethyl)-1-tosylpiperidine-2,6-diyl)dimethanol (0.8 g, 2.25 mmol) in pyridine (2 mL) was added TsCl (1 g, 2.3 mmol). The mixture was stirred for 3 h and poured into a mixture of 1N HCl and EtOAc. The organic phase was washed 3× with 1N HCl, then saturated aq. sodium bicarbonate, dried over sodium sulfate, filtered and evaporated to afford ((2R,4s,6S)-4-(azidomethyl)-1-tosylpiperidine-2,6-diyl)bis(methylene) bis(4-methylbenzenesulfonate) (1.03 g, 1.554 mmol, 68.8% yield). LCMS Method A: retention time=4.33 min, M+H=663.14. $^1$H NMR (400 MHz, CHLOROFORM-d) δ=7.84 (d, J=8.3 Hz, 4H), 7.75-7.58 (m, 2H), 7.41 (d, J=8.0 Hz, 4H), 7.35-7.30 (m, 2H), 4.11-3.90 (m, 6H), 2.95 (d, J=6.5 Hz, 2H), 2.50 (s, 6H), 2.45 (s, 3H), 1.86-1.74 (m, 2H), 1.18-1.00 (m, 2H), 0.72 (d, J=4.8 Hz, 1H).

Step E: 4-tosyl-1,4-diazaadamantane

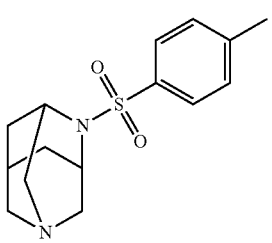 [SMILES: Cc1ccc(S(=O)(=O)N2C3CC4CC2CN(C4)C3)cc1]

A flask was charged with (4-(azidomethyl)-1-tosylpiperidine-2,6-diyl)bis(methylene) bis(4-methylbenzenesulfonate) (165 mg, 0.249 mmol) in THF (5 ml). The mixture was azeotroped with toluene to remove residual moisture and then flushed with nitrogen, at which point trimethylphosphine (0.4 ml, 0.400 mmol) was added. After ~3 h, the reaction was quenched with aq. saturated sodium bicarbonate. The mixture was allowed to stir for 3d at rt. The reaction mixture was diluted with water and most of the THF was evaporated on the rotovap. The mixture was extracted with chloroform 3× and the chloroform extracts were washed with brine, dried over sodium sulfate, filtered and evaporated. The crude residue was purified by silica gel chromatography on a 25 g col, 5-40% (9:1 MeOH/NH₄OH)/Chloroform over 10 CV, affording (1r,3R,5S,7s)-4-tosyl-1,4-diazaadamantane (44.5 mg, 0.152 mmol, 61.1% yield). LCMS Method A: retention time=2.78 min, M+H=293.14. $^1$H NMR (400 MHz, CHLOROFORM-d) δ=7.79-7.73 (m, 2H), 7.31 (d, J=8.0 Hz, 2H), 3.89 (br. s., 2H), 3.24-3.13 (m, 4H), 3.08-2.99 (m, 2H), 2.47-2.41 (m, 3H), 2.03 (d, J=12.0 Hz, 2H), 1.92-1.85 (m, 2H), 1.82 (br. s., 1H).

In an alternate procedure, 4-tosyl-1,4-diazaadamantane was also prepared by the following method: (4-(azidomethyl)-1-tosylpiperidine-2,6-diyl)bis(methylene) bis(4-methylbenzenesulfonate) (1.15 g, 1.735 mmol) was taken in 2-butanol (10 mL). The solids were insufficiently soluble, so ethyl acetate (50 mL) was added and the mixture was transferred to a 500 mL Parr bottle containing 100 mg 10% Pd/C. The mixture was hydrogenated 30 min at 55 psi. TLC showed no reaction, so ethanol (50 ml) was added and the mixture hydrogenated 1.5 h at 55 psi. TLC again showed no reaction, so 300 mg more catalyst and return to hydrogenator overnight. TLC showed complete consumption of starting material (azide reduction) with the major component being the amine. The mixture was filtered through celite, washed with EtOAc, then EtOH and most of the solvent was evaporated. The residue was diluted with ~30 mL 2-butanol, K2CO3 (800 mg) was added and the mixture was heated to reflux on a 110 C oil bath. After 4 h, the mixture was evaporated to dryness, water was added, the mixture was extracted with chloroform 3×, dried over sodium sulfate, filtered and evaporated. The crude residue was purified by silica gel chromatography on a 40 g column, eluting with a gradient of 2-40% (9:1 MeOH/NH4OH) in chloroform to provide 4-tosyl-1,4-diazaadamantane (170 mg, 34% yield). $^1$H NMR (400 MHz, CHLOROFORM-d) δ=7.76 (d, J=8.3 Hz, 2H), 7.32 (d, J=8.0 Hz, 2H), 3.95 (br. s., 2H), 3.21 (br. s., 4H), 3.13-3.02 (m, 2H), 2.45 (s, 3H), 2.04 (br. s., 2H), 1.90 (br. s., 3H).

Step F: tert-butyl 1,4-diazaadamantane-4-carboxylate

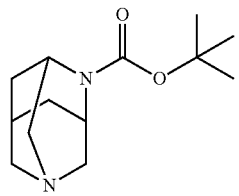 [SMILES: CC(C)(C)OC(=O)N1C2CC3CC1CN(C3)C2]

Naphthalene (66 mg, 0.515 mmol) was dissolved in THF (2.5 mL) and sodium (26 mg, 1.131 mmol) (cut into small pieces) was added. There was no reaction after 15 min, at which point the sodium in the solution was broken up with the aid of tweezers. The mixture immediately began to turn green and was allowed to age 30 min, affording a deep green color. In a separate flask, (1r,3R,5S,7s)-4-tosyl-1,4-diazaadamantane (54 mg, 0.185 mmol) was dissolved in THF (1 mL) and cooled to −78° C. The solution of sodium naphthalenide was added dropwise until green color persists, and then was stirred an additional 15 min at same temperature, quenched by addition of 0.2 mL saturated aq. ammonium chloride and allowed to warm to rt. Sodium sulfate was added and the mixture was diluted with chloroform and filtered. Di-tert-butyl dicarbonate (0.043 mL, 0.185 mmol) was added and the mixture stirred for 30 min, the solvent evaporated and the crude residue was purified by silica gel chromatography eluting with 5-40% (9:1 MeOH/NH4OH) in chloroform to afford tert-butyl 1,4-diazaadamantane-4-carboxylate (19 mg, 43% yield). LCMS Method B: Retention time=2.89 min, M+H=239.1. $^1$H NMR (400 MHz, CHLOROFORM-d) δ=4.19 (br. s., 1H), 4.11-4.02 (m, 1H), 3.29 (s, 6H), 1.97 (br. s., 5H), 1.50 (s, 9H).

Step G: 1,4-diazaadamantane, 2TFA

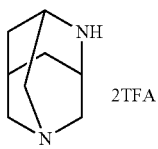

Tert-butyl 1,4-diazaadamantane-4-carboxylate (19 mg, 0.080 mmol) was dissolved in chloroform (1 mL) and TFA (1 ml, 12.98 mmol) was added. The mixture was aged 30 min, evaporated and azeotroped with chloroform 2× to afford 1,4-diazaadamantane, 2TFA quantitative yield was assumed for the purpose of calculating stoichiometry for the next step. $^1$H NMR (400 MHz, METHANOL-$d_4$) δ=4.09 (br. s., 2H), 3.93-3.83 (m, 4H), 3.77 (d, J=2.0 Hz, 2H), 2.49 (br. s., 1H), 2.38-2.29 (m, 4H).

Step H:
1,4-diazaadamantan-4-yl(1H-indazol-3-yl)methanone

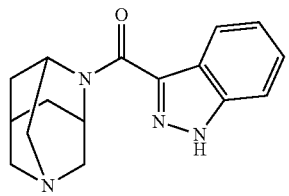 [SMILES: O=C(c1n[nH]c2ccccc12)N1C2CC3CC1CN(C3)C2]

A flask was charged with 1,4-diazaadamantane, 2TFA (29 mg, 0.08 mmol), DMF (1 mL), 1H-indazole-3-carboxylic acid (16 mg, 0.096 mmol), HATU (38 mg, 0.10 mmol) and DIPEA (0.08 mL, 0.44 mmol) were added. The mixture was allowed to stir at ambient temperature overnight. The solvent was removed by evaporation under a stream of nitrogen, and the residue was partitioned between chloroform and saturated aqueous sodium bicarbonate. The phases were separated and the aqueous fraction extracted twice more with chloroform. The combined organic phases were dried over sodium sulfate, filtered and the solvent was removed by evaporation on the rotovap. The resultant residue was purified by silica gel chromatography, eluting with a gradient from 5% to 40% (9:1 MeOH/NH4OH) in chloroform, affording the title compound (8.2 mg, 35% yield). LCMS METHOD A: retention time=2.62 min, M+H=283.2. $^1$H NMR (500 MHz, CHLOROFORM-d) δ=10.57-10.32 (m, 1H), 8.16 (td, J=0.9, 8.2 Hz, 1H), 7.58-7.51 (m, 1H), 7.50-7.41 (m, 1H), 7.34-7.29 (m, 1H), 4.88 (br. s., 2H), 3.46-3.29 (m, 5H), 3.20 (d, J=13.2 Hz, 1H), 2.20 (s, 3H), 2.01 (br. s., 2H).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:
1. A compound of formula I

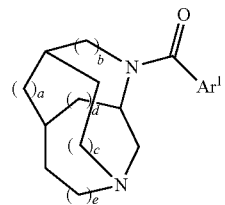

where:
$Ar^1$ is selected from the group consisting of phenyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, pyridinyl, pyridazinyl, pyrimidinyl, pyrazinyl, naphthalenyl, indolyl, indazolyl, benzofuranyl, dihydrobenzofuranyl, benzodioxolanyl, benzothiophenyl, dihydrobenzothiophenyl, benzoisothiazolyl, benzothiazolyl, thienopyrazinyl, pyrrolopyridinyl, benzoisoxazolyl, quinolinyl, isoquinolinyl, quinoxalinyl, and naphthyridinyl, and is substituted with 0-3 substituents selected from the group consisting of cyano, halo, alkyl, haloalkyl, cycloalkyl, alkoxy, haloalkoxy, alkylthio, and $Ar^2$;
$Ar^2$ is phenyl substituted with 0-3 substituents selected from cyano, halo, alkyl, haloalkyl, alkoxy, and haloalkoxy; and
a is 0, b is 1, c is 0, d is 0, and e is 1; or
a is 0, b is 1, c is 1, d is 0, and e is 1; or
a is 1, b is 0, c is 0, d is 1, and e is 0;
or a pharmaceutically acceptable salt thereof.
2. A compound of claim 1 where:
$Ar^1$ is selected from the group consisting of phenyl, furanyl, thienyl, isoxazolyl, isothiazolyl, imidazolyl, thiazolyl, thiadiazolyl, thiazinyl, pyridinyl, pyridazinyl, pyrimidinyl, pyrazinyl, naphthalenyl, indolyl, indazolyl, benzofuranyl, dihydrobenzofuranyl, benzodioxolanyl, benzothiophenyl, dihydrobenzothiophenyl, benzoisothiazolyl, benzothiazolyl, thienopyrazinyl, pyrrolopyridinyl, benzoisoxazolyl, quinolinyl, quinoxalinyl, and naphthyridinyl, and is substituted with 0-2 substituents selected from the group consisting of cyano, halo, alkyl, haloalkyl, cycloalkyl, alkoxy, haloalkoxy, alkylthio, and $Ar^2$; and
$Ar^2$ is phenyl substituted with 0-3 substituents selected from cyano, halo, alkyl, haloalkyl, alkoxy, and haloalkoxy;
or a pharmaceutically acceptable salt thereof.
3. A compound of claim 2 where:
$Ar^1$ is selected from the group consisting of phenyl, furanyl, thienyl, isoxazolyl, isothiazolyl, imidazolyl, thiazolyl, thiadiazolyl, thiazinyl, triazinyl, pyridinyl, pyridazinyl, pyrimidinyl, pyrazinyl, naphthalenyl, indolyl, indazolyl, benzofuranyl, dihydrobenzofuranyl, benzodioxolanyl, benzothiophenyl, dihydrobenzothiophenyl, benzoisothiazolyl, benzothiazolyl, thienopyrazinyl, pyrrolopyridinyl, benzoisoxazolyl, quinolinyl, quinoxalinyl, and naphthyridinyl, and is substituted with 0-2 substituents selected from the group consisting of halo, alkyl, haloalkyl, alkoxy, alkylthio, and $Ar^2$; and
$Ar^2$ is phenyl substituted with 0-1 halo;
or a pharmaceutically acceptable salt thereof.

4. A compound of claim 1 where a is 0, b is 1, c is 0, d is 0, and e is 1.

5. A compound of claim 1 where a is 0, b is 1, c is 1, d is 0, and e is 1.

6. A compound of claim 1 where a is 1, b is 0, c is 0, d is 1, and e is O.

7. A compound of claim 1 where Ar¹ is indazolyl substituted with 0-3 substituents selected from the group consisting of cyano, halo, alkyl, haloalkyl, cycloalkyl, alkoxy, and haloalkoxy; or a pharmaceutically acceptable salt thereof.

8. A compound of claim 1 selected from the group consisting of

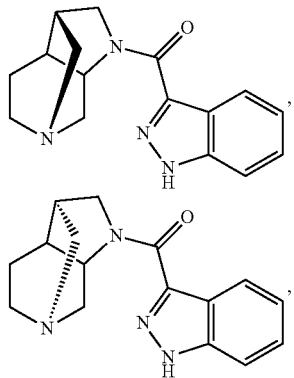

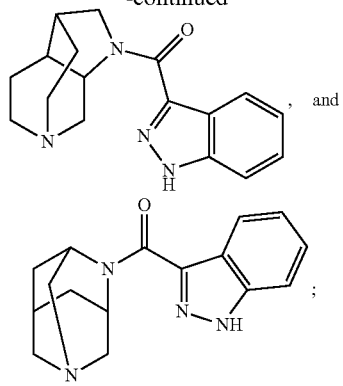

or a pharmaceutically acceptable salt thereof.

9. A pharmaceutical composition comprising a therapeutically effective amount of a compound of claim 1, or a pharmaceutically acceptable salt thereof, and a pharmaceutically acceptable carrier.

10. A method for the treatment of schizophrenia, Alzheimer's Disease, cognitive disorders, rheumatoid arthritis, osteoarthritis, ulcerative colitis, Crohn's Disease, or diabetes which comprises administering to a patient a therapeutically affective amount of a compound of claim 1.

11. The method of claim 10 directed to schizophrenia.

12. The method of claim 10 directed to Alzheimer's Disease.

* * * * *

UNITED STATES PATENT AND TRADEMARK OFFICE
CERTIFICATE OF CORRECTION

PATENT NO. : 9,708,323 B2  
APPLICATION NO. : 15/317546  
DATED : July 18, 2017  
INVENTOR(S) : McDonald et al.

Page 1 of 1

It is certified that error appears in the above-identified patent and that said Letters Patent is hereby corrected as shown below:

In the Claims

Claim 6, Column 101, Line 6:
Delete "O." and insert -- 0. --.

Signed and Sealed this
Eighteenth Day of September, 2018

Andrei Iancu
*Director of the United States Patent and Trademark Office*